United States Patent [19]

Kamiya et al.

[11] 4,350,692

[45] Sep. 21, 1982

[54] 3,7-DISUBSTITUTED-3-CEPHEM-4-CARBOXYLIC ACIDS

[75] Inventors: Takashi Kamiya, Suita; Tsutomu Teraji, Toyonaka, both of Japan

[73] Assignee: Fujisawa Pharmaceutical Co., Ltd., Osaka, Japan

[21] Appl. No.: 922,384

[22] Filed: Jul. 6, 1978

Related U.S. Application Data

[63] Continuation-in-part of Ser. No. 802,871, Jun. 2, 1977, abandoned, and a continuation-in-part of Ser. No. 802,957, Jun. 2, 1977, abandoned, and a continuation-in-part of Ser. No. 802,976, Jun. 2, 1977, abandoned.

[30] Foreign Application Priority Data

Jun. 3, 1976 [JP] Japan .................................. 51/65377
Aug. 19, 1976 [JP] Japan .................................. 51/99315
Sep. 6, 1976 [JP] Japan .................................. 51/106887

[51] Int. Cl.$^3$ ................... A61K 31/545; C07D 501/54
[52] U.S. Cl. ..................................... 424/246; 544/26; 544/27; 544/29; 544/30

[58] Field of Search ........................... 424/246; 544/26

[56] References Cited

U.S. PATENT DOCUMENTS

| 3,352,858 | 11/1967 | Crast et al. | 544/26 |
| 3,931,170 | 1/1976 | Treuner et al. | 544/26 |
| 4,039,536 | 8/1977 | Takano et al. | 544/26 |

FOREIGN PATENT DOCUMENTS

| 833063 | 4/1976 | Belgium . |
| 51-65377 | 3/1976 | Japan . |

OTHER PUBLICATIONS

Iwanami et al., Chem. Abstr., (1976), vol. 85:160,128(f).

*Primary Examiner*—Paul M. Coughlan, Jr.
*Attorney, Agent, or Firm*—Dayton R. Stemple

[57] ABSTRACT

Preparation of pharmaceutical composition comprising, treatment of human and animal diseases with, and compounds of, 3,7-disubstituted-3-cephem-4-carboxylic acid.

9 Claims, No Drawings

3,7-DISUBSTITUTED-3-CEPHEM-4-CARBOXYLIC ACIDS

This application is a combined continuation-in-part of co-pending applications, Ser. Nos. 802,871, 802,957 and 802,976, all filed June 2, 1977 and now abandoned.

The present invention relates to new 3,7-disubstituted-3-cephem-4-carboxylic acids and pharmaceutically acceptable salts thereof. More particularly, it relates to new 3,7-disubstituted-3-cephem-4-carboxylic acids and pharmaceutically acceptable salts thereof which have antibacterial activities and to pharmaceutical composition comprising the same.

Accordingly, it is an object of the present invention to provide 3,7-disubstituted-3-cephem-4-carboxylic acids and pharmaceutically acceptable salts thereof, which are highly active against a number of pathogenic bacteria.

Another object of the present invention is to provide pharmaceutical composition comprising, as an active ingredient, said 3,7-disubstituted-3-cephem-4-carboxylic acid or pharmaceutically acceptable salt thereof.

The objective 3,7-disubstituted-3-cephem-4-carboxylic acids can be represented by the following formula (I):

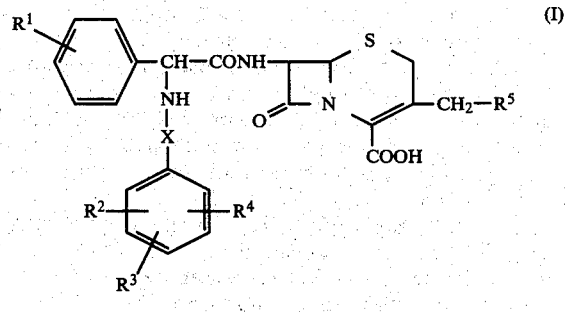

wherein
(i)
$R^1$ is hydrogen, hydroxy or lower alkanesulfonamido,
$R^2$ is halogen, hydroxy, carboxy, sulfo, nitro, lower alkoxy, lower alkylthio, lower alkanoyloxy, lower alkanoylthio or lower alkanesulfonamide, each of which is always attached to the ortho-position of the benzene ring,
$R^3$ and $R^4$ are each, same or different, hydrogen, halogen, nitro, sulfamoyl, carbamoyl, hydroxy, cyano, amino, sulfo, halosulfonyl, lower alkanoyl, lower alkanamido, lower alkylsulfamoyl, arylsulfamoyl or 4-(lower)alkylpiperazine-1-sulfonyl,
$R^5$ is hydrogen, lower alkanoyloxy or heterocyclic-thio, in which the heterocyclic moiety may be substituted with lower alkyl, amino(lower)alkyl, acylamino or acylamino(lower)alkyl, and
X is carbonyl, sulfonyl or methylene,
(ii)
$R^1$ $R^2$, $R^3$ and $R^4$ are each hydrogen,
$R^5$ is lower alkanoyloxy or heterocyclic-thio, in which the heterocyclic moiety may be substituted with lower alkyl, and
X is lower alkylenecarbonyl, in which the lower alkylene moiety is substituted with hydroxy, amino, sulfo, hydroxyimino or acylamino, or
(iii)
$R^1$ is hydrogen or lower alkanesulfonamido,
$R^2$ is hydroxy, amino(lower)alkyl, protected amino(lower)alkyl, nitro or acyl,
$R^3$ and $R^4$ are each, same or different, hydrogen, halogen, hydroxy, amino(lower)alkyl, protected amino(lower)alkyl, nitro or acyl,
$R^5$ is lower alkanoyloxy or heterocyclic-thio, in which the heterocyclic moiety may be substituted with lower alkyl, and
X is lower alkenylenecarbonyl or -O-(lower)alkylenecarbonyl, provided that when $R^2$ is nitro and $R^3$ and $R^4$ are each, same or different, hydrogen or halogen, then X is lower alkenylenecarbonyl,
or its derivative at the carboxy group, or the nontoxic pharmaceutically acceptable salt thereof.

In the above and subsequent descriptions of the present specification, suitable examples and illustration of the various definitions which the present invention intends to include within the scope thereof are explained in detail as follows.

The term "lower" is used to intend a group having 1 to 6 carbon atoms, unless otherwise provided.

"Lower alkoxy" for $R^2$ may include straight or branched one having 1 to 6 carbon atoms, such as methoxy, ethoxy, propoxy, isopropoxy, butoxy, isobutoxy, t-butoxy, pentyloxy, hexyloxy or the like, and preferably one having up to 4 carbon atoms and more preferably one having 1 to 2 carbon atoms.

"Lower alkylthio" for $R^2$ may include straight or branched one having up to 6 carbon atoms, such as methylthio, ethylthio, propylthio, isopropylthio, butylthio, isobutylthio, t-butylthio, pentylthio, neopentylthio, hexylthio, or the like, and preferably one having up to 4 carbon atoms.

"Lower alkanoyl" for $R^3$ and $R^4$, and "lower alkanoyl" moiety in the lower alkanoyloxy for $R^2$ and $R^5$, lower alkanoylthio for $R^2$ and lower alkanamido for $R^3$ and $R^4$ may include alkanoyl derived from the lower alkanoic acid having up to 7 carbon atoms, such as formyl, acetyl, propionyl, butyryl, isobutyryl, valeryl, isovaleryl, oxalyl, succinyl, pivaloyl or the like, and preferably lower alkanoyl having up to 3 carbon atoms.

Accordingly, "lower alkanoyloxy" for $R^2$ and $R^5$ may include formyloxy, acetyloxy, propionyloxy, butyryloxy, isobutyryloxy, valeryloxy, isovaleryloxy, oxalyloxy, succinyloxy, pivaloyloxy and the like, "lower alkanoylthio" for $R^2$ may include formylthio, acetylthio, propionylthio, butyrylthio, isobutyrylthio, valerylthio, isovalerylthio, oxalylthio, succinylthio, pivaloylthio and the like, and "Lower alkanamido" for $R^3$ and $R^4$ may include an amino group substituted with the lower alkanoyl, such as formamido, acetamido, propionamido, butyramido, isobutyramido, valeramido, isovaleramido, oxalamido, succinamido, pivalamido or the like.

"Lower alkanesulfonamido" for $R^1$ and $R^2$ may include an amino group substituted with lower alkanesulfonyl group, such as mesylamino, ethanesulfonamido, propanesulfonamido, butanesulfonamido, pentanesulfonamido, hexanesulfonamido and the like.

"4-(Lower)alkylpiperazine-1-sulfonyl" for $R^3$ and $R^4$ may include 4-lower alkyl-substituted piperazine-1-sulfonyl group such as 4-methylpiperazine-1-sulfonyl, 4-ethylpiperazine-1-sulfonyl, 4-propylpiperazine-1-sulfonyl, 4-isopropylpiperazine-1-sulfonyl, 4-butylpiperazine-1-sulfonyl, 4-pentylpiperazine-1-sulfonyl, 4-hexylpiperazine-1-sulfonyl and the like.

"Lower alkylsulfamoyl" for $R^3$ and $R^4$ may include a sulfamoyl group substituted with one or two alkyl groups such as N-lower alkyl sulfamoyl (e.g. N-methylsulfamoyl, N-ethylsulfamoyl, N-propylsulfamoyl, N-isopropylsulfamoyl, N-butylsulfamoyl, N-pentylsulfamoyl, N-hexylsulfamoyl, etc.) or N,N-di(lower)alkylsulfamoyl (e.g. N,N-dimethylsulfamoyl, N,N-diethylsulfamoyl, N-methyl-N-ethylsulfamoyl, N,N-dipropylsulfamoyl, N,N-dibutylsulfamoyl, N,N-dipentylsulfamoyl, N,N-dihexylsulfamoyl, etc.).

"Arylsulfamoyl" for $R^3$ and $R^4$ may include a sulfamoyl group substituted with aryl, such as phenylsulfamoyl, tolylsulfamoyl, xylylsulfamoyl, naphthylsulfamoyl or the like.

"Halogen" for $R^2$, $R^3$ and $R^4$ and halogen of halosulfonyl for $R^3$ and $R^4$ may include chlorine, bromine, iodine and fluorine.

"Halosulfonyl" for $R^3$ and $R^4$ may include chlorosulfonyl, bromosulfonyl, iodosulfonyl and the like.

Heterocyclic group in the "heterocyclic-thio" group for $R^5$ may include saturated or unsaturated, mono- or poly-cyclic heterocyclic group containing at least one hetero-atom such as an oxygen, sulfur or nitrogen atom.

Among the said heterocyclic group, preferable heterocyclic group may be N-containing heterocyclic group such as:

unsaturated 5 to 6-membered heteromonocyclic group containing 1 to 4 nitrogen atoms, for example, pyrrolyl, pyrrolinyl, imidazolyl, pyrazolyl, pyridyl and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.);

saturated 5 to 6-membered heteromonocyclic group containing 1 to 4 nitrogen atoms (e.g., pyrrolidinyl, imidazolidinyl, piperidino, piperazinyl, etc.);

unsaturated, 9 to 10 membered, condensed heterocyclic group containing 1 to 4 nitrogen atoms (e.g., indolyl, isoindolyl, indolizynyl, benzimidazolyl, quinolyl, isoquinolyl, indazolyl, benzotriazolyl, etc.);

unsaturated 5 to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.);

saturated 5 to 6-membered heteromonocyclic group containing 1 to 2 oxygen atoms and 1 to 3 nitrogen atoms (e.g., morpholinyl, etc.);

unsaturated 9 to 10 membered, condensed heterocyclic group containing 1 to 2 oxygen atoms and 1 to 3 nitrogen atoms (e.g., benzoxazolyl, benzoxadiazolyl, etc.);

unsaturated 5 to 6-membered heteromonocyclic group containing 1 to 2 sulfur atoms and 1 to 3 nitrogen atoms, for example, thiazolyl, isothiazolyl, thiadiazolyl (e.g., 1,2,4-thiadiazolyl, 1,3,4-thiadiazolyl, 1,2,5-thiadiazolyl, etc.);

saturated 5 to 6-membered heteromonocyclic group containing 1 to 2 sulfur atoms and 1 to 3 nitrogen atoms (e.g., thiazolidinyl, etc.);

unsaturated, 9 to 10-membered condensed heterocyclic group containing 1 to 2 sulfur atoms and 1 to 3 nitrogen atoms (e.g., benzothiazolyl, benzothiadiazolyl, etc.), and the like.

The heterocyclic group as mentioned above may be substituted optionally with one or more substituents selected from lower alkyl, amino(lower)alkyl, acylamino and acylamino(lower)alkyl. Among these substituents, "lower alkyl" may include straight or branched aliphatic hydrocarbon residue having up to six carbon atoms, such as methyl, ethyl, propyl, isopropyl, butyl, isobutyl, t-butyl, pentyl, neopentyl, hexyl, and the like. Amino(lower)alkyl may include aminomethyl, aminoethyl, aminopropyl, aminobutyl, aminopentyl, aminohexyl and the like.

"Acyl" for $R^2$, $R^3$ and $R^4$ and "acyl" moiety of acylamino or acylamino(lower)alkyl, each of which is a substituent on the heterocyclic-thio group for $R^5$ may include an acyl radical derived from an acid such as carboxylic, sulfonic, carbamic or carbonic acid including substituted or unsubstituted carbamoyl, aliphatic acyl, and acyl having an aromatic ring or heterocyclic ring.

Suitable examples of the aliphatic acyl derived from an aliphatic acid may be lower alkanoyl (e.g. formyl, acetyl, propionyl, butyryl, isobutyryl, isovaleryl, oxalyl, succinyl, pivaloyl, etc.); lower alkoxycarbonyl (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.); lower alkoxyalkanoyl (e.g., methoxyacetyl, ethoxyacetyl, methoxypropionyl, etc.); and lower alkanesulfonyl, (e.g., mesyl, ethanesulfonyl, methylethanesulfonyl, butanesulfonyl, etc.).

Suitable examples of the acyl having an aromatic ring i.e. aromatic acyl derived an acid containing an aromatic ring may be ar(lower)alkanoyl (e.g., phenylacetyl, phenylpropionyl, etc.); ar(lower)alkoxycarbonyl (e.g., benzyloxycarbonyl, phenethyloxycarbonyl, etc.); aroyl (e.g., benzoyl, toluoyl, naphthoyl, phthaloyl, indancarbonyl, etc.); aryloxy(lower)alkanoyl (e.g. phenoxyacetyl, etc.) and arenesulfonyl (e.g., benzenesulfonyl, tosyl, etc.).

Suitable example of the acyl having a heterocyclic ring i.e. heterocyclic acyl derived from an acid containing a heterocyclic ring may be heterocycle(lower)alkanoyl (e.g., thienylacetyl, furylacetyl, pyrrolylacetyl, thiadiazolylacetyl, tetrazolylacetyl, etc.); heterocyclecarbonyl (e.g., thenoyl, furoyl, nicotinoyl, isonicotinoyl, pyrrolecarbonyl, etc.).

Suitable substituted or unsubstituted carbamoyl may include carbamoyl, N-lower alkylcarbamoyl (e.g., N-methylcarbamoyl, N-ethylcarbamoyl, etc.), N-arylcarbamoyl (e.g., N-phenylcarbamoyl, etc.), N-(substituted or unsubstituted lower alkanoyl)carbamoyl (e.g., N-acetylcarbamoyl, N-trichloroacetylcarbamoyl, etc.) and the like.

The acyl moiety as stated above (especially, alkane moiety, arene moiety and heterocycle moiety in the acyl) may have optionally 1 to 3 suitable substituents such as halogen (e.g., chlorine, bromine, iodine or fluorine), hydroxy, cyano, nitro, carboxy, sulfo, lower alkoxy, lower alkyl, lower alkenyl, acyl (e.g. chloroacetyl, dichloroacetyl, trichloroacetyl, trifluoroacetyl, etc.), aryl (e.g., phenyl, tolyl, etc.), and the like.

Accordingly, suitable acylamino may be an amino group substituted with acyl moiety as mentioned above, such as lower alkanoyl (e.g., formyl, acetyl, propionyl, butyryl, valeryl, isovaleryl, pivaloyl, hexanoyl, etc.), lower alkanesulfonyl (e.g., mesyl, ethanesulfonyl, propanesulfonyl, butanesulfonyl, pentanesulfonyl, hexanesulfonyl, etc.) or the like and the said acyl moiety may be substituted with carboxy, sulfo and the like.

Further, suitable acylamino(lower)alkyl may be amino(lower)alkyl mentioned above substituted with the acyl moiety described above, such as lower alkanoylamino(lower)alkyl, (e.g. acetamidomethyl, acetamidoethyl, acetamidopropyl, propionamidomethyl, propionamidoethyl, propionamidopropyl, etc.), lower alkanesulfonamido(lower)alkyl (e.g. methanesulfonamidomethyl, ethanesulfonamidomethyl, ethanesulfonamidoethyl, propanesulfonamidoethyl etc.) and the said acyl moiety may be further substituted with sulfo, carboxy, lower alkoxycarbonyl (e.g., methoxycarbonyl, ethoxycarbonyl, propoxycarbonyl, isopropoxycarbonyl, butoxycarbonyl, pentyloxycarbonyl, etc.), or the like.

Suitable "lower alkylenecarbonyl" and lower alkylenecarbonyl moiety of -O-(lower)alkylenecarbonyl for X may include methylenecarbonyl, ethylenecarbonyl, 1-methylethylenecarbonyl trimethylenecarbonyl; propylenecarbonyl, tetramethylenecarbonyl, pentamethylenecarbonyl and the like, and it is to be noted that said lower alkylenecarbonyl for X in the definition (ii) is always substituted with hydroxy, amino, sulfo, hydroxyimino or acylamino group, and the acylamino group may include the ones as illustrated before.

Suitable "alkenylenecarbonyl" for X may include vinylenecarbonyl, propenylenecarbonyl and the like.

Suitable "amino(lower)alkyl" for $R^2$, $R^3$ and $R^4$ is the same as illustrated before.

Suitable protective group of "protected amino(lower)alkyl" for $R^2$ may include an acyl mentioned above and a conventional protective group such as aralkyl (e.g. benzyl, benzhydryl, etc.) or the like.

The derivative at the carboxy group of the object compound (I) may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.);

mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester, etc.);

ar(lower)alkyl ester, for example, phenyl(lower)alkyl ester which may have one or more suitable substituents (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-t-butylbenzyl ester, etc.);

aryl ester which may have one or more suitable substituents (e.g., phenyl ester, tolyl ester, t-butylphenyl ester, xylyl ester, mesityl ester, cumenyl ester, etc.);

an ester with silyl compound, for example, tri(lower)alkyl silyl ester, and the like.

Suitable pharmaceutically acceptable salt of the object compound (I) is conventional non-toxic salt and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc.;

an organic salt, for example, an organic amine salt (e.g., trimethylamine salt, triethylamine salt, pyridine salt, picoline salt, dicyclohexylamine salt, N,N'-dibenzylethylenediamine salt, N-methylglucamine salt, diethanolamine salt, triethanolamine salt, tris(hydroxymethylamino)methane salt, etc.) etc.;

an organic carboxylic or sulfonic acid salt (e.g., acetate, maleate, tartrate, methanesulfonate, benzenesulfonate, toluenesulfonate, etc.);

an inorganic acid salt (e.g., hydrochloride, hydrobromide, sulfate, phosphate, etc.);

a salt with a basic or acidic amino acid (e.g., arginine, aspartic acid, glutamic acid, etc.), and the like.

The object compound (I) of the present invention can be prepared according to several conventional methods which are well known and applied in the field of cephalosporin chemistry, and explained briefly in the following.

The main processes among them are shown in the following scheme.

PROCESS 1

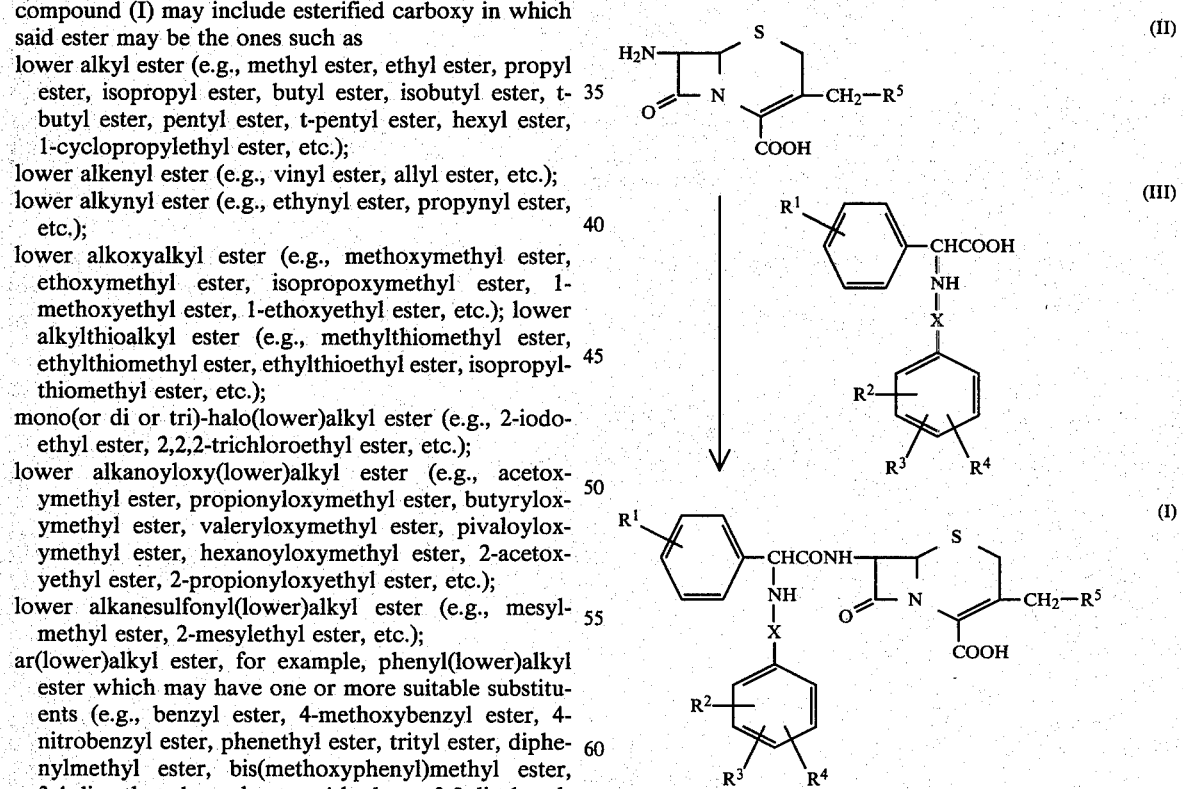

wherein $R^1$, $R^2$, $R^3$, $R^4$ and $R^5$ are each as defined in the definitions (i), (ii) and (iii).

PROCESS 2

(1)

-continued
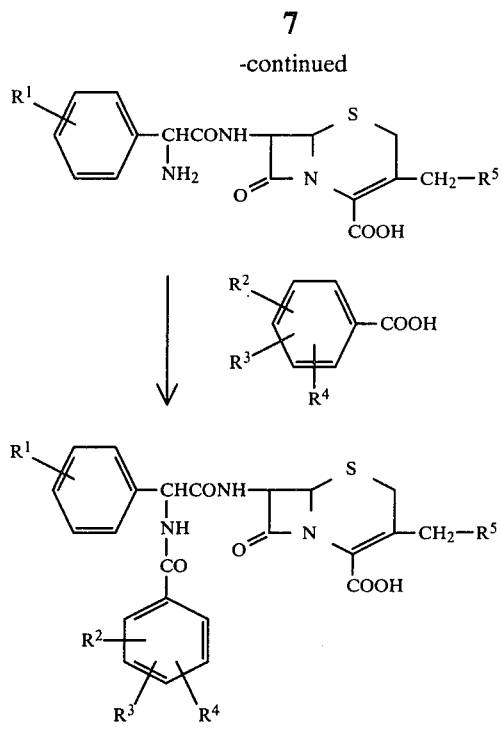
wherein $R^1$, $R^2$, $R^3$, $R^4$ and $R^5$ are each as defined in the definition (i).
(2)
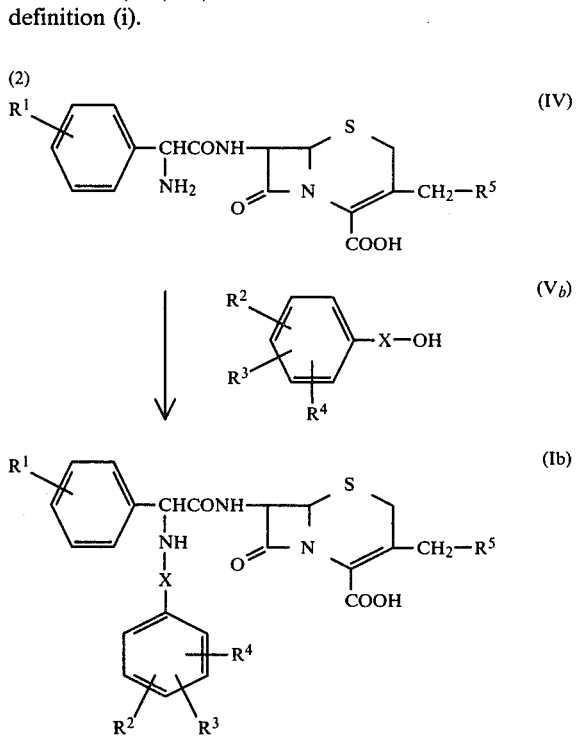
wherein $R^1$, $R^2$, $R^3$, $R^4$, $R^5$ and X are each as defined in the definitions (ii) and (iii).
(3)
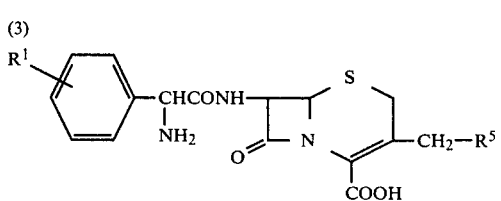
-continued
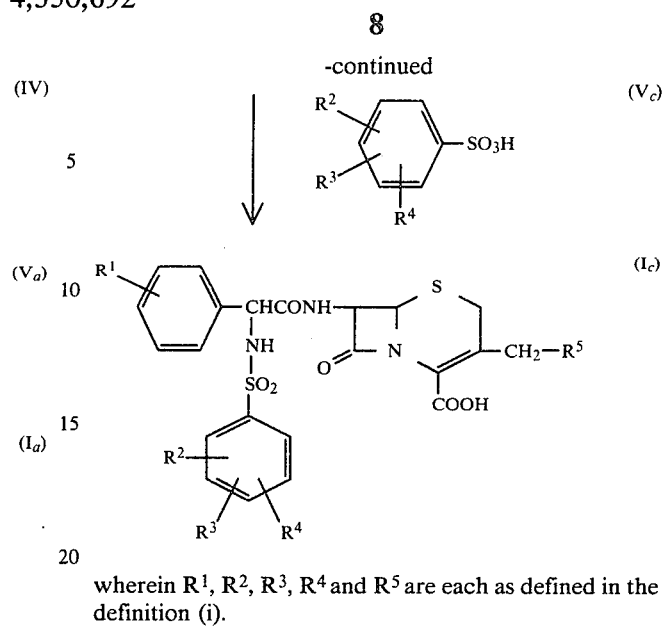
wherein $R^1$, $R^2$, $R^3$, $R^4$ and $R^5$ are each as defined in the definition (i).
PROCESS 3
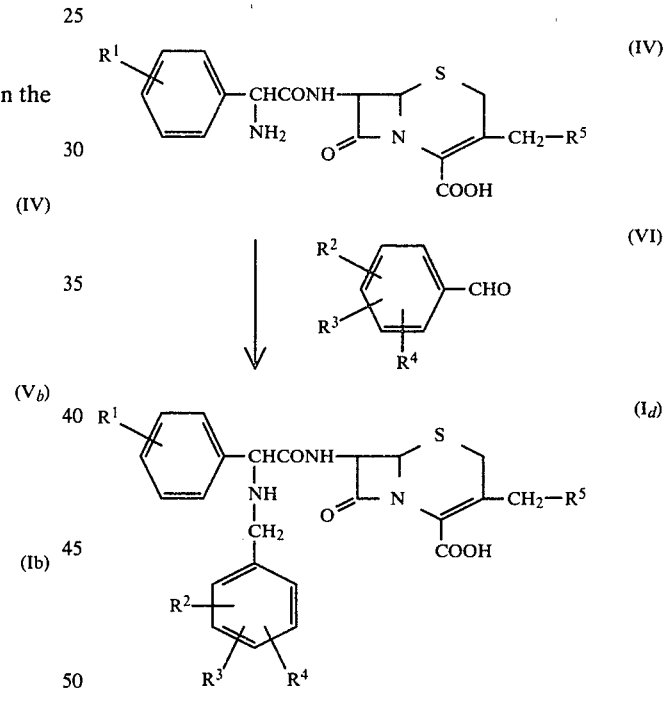
wherein $R^1$, $R^2$, $R^3$, $R^4$ and $R^5$ are each as defined in the definition (i).
PROCESS 4
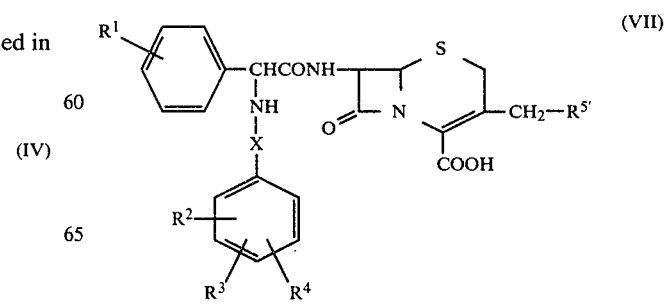

-continued

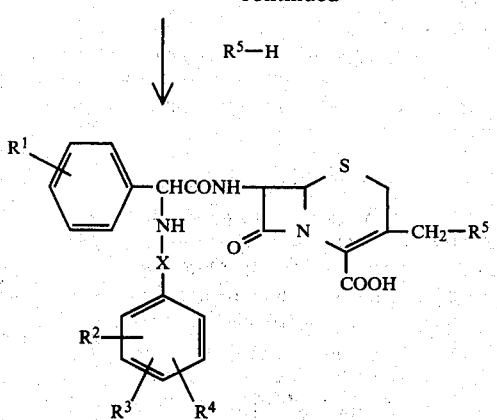

wherein
$R^1$, $R^2$, $R^3$, $R^4$ and X are each as defined in the definitions (i), (ii) and (iii),
$R^{5'}$ is lower alkanoyloxy, and
$R^5$ is heterocyclic-thio in which the heterocyclic moiety may be substituted as defined in the definitions (i), (ii) and (iii).

PROCESS 5

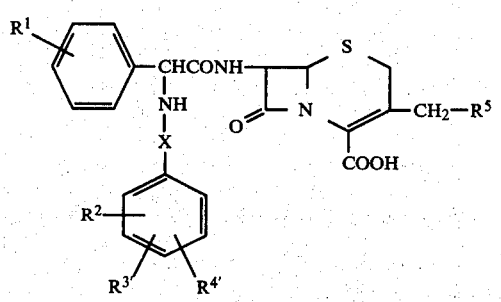

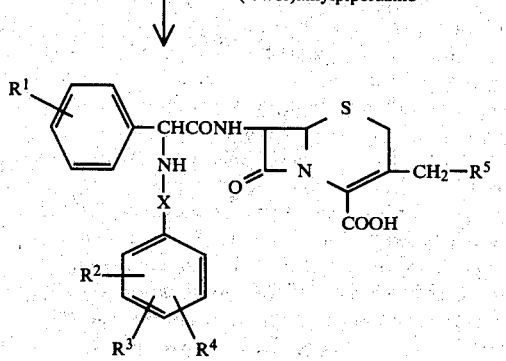

wherein
$R^1$, $R^2$, $R^5$ and X are each as defined in the definition (i), one of $R^3$ and $R^4$ is 4-(lower)alkylpiperazine-1-sulfonyl and another is as defined in the definition (i), and
one of $R^{3'}$ and $R^{4'}$ is halosulfonyl and another is the same as $R^3$ and $R^4$ in the definition (i).

PROCESSES 1 AND 2

Processes 1 and 2 are concerned with N-acylation, the former being acylation of amino group at the 7th position of 3-cephem nucleus and the latter being acylation of the α-amino group, and accordingly the acylation reaction can be conducted in the substantially same manner.

The reaction is usually carried out in a conventional solvent such as water, acetone, dioxane, acetonitrile, chloroform, methylene chloride, ethylene chloride, tetrahydrofuran, ethyl acetate, N,N-dimethyl-formamide, pyridine or the like, under cooling or at ambient temperature.

When the starting compound (III), ($V_a$), ($V_b$) and ($V_c$) are free acid or its salt form in the reaction, the reaction is preferably carried out in the presence of a conventional condensing agent.

The reaction may also be carried out in the presence of an inorganic or an organic base.

The reaction is preferably conducted by activating the carboxy radical of the starting compounds (III), ($V_a$) and ($V_b$) and the sulfonyl radical of the compound ($V_c$) in the form of the reactive derivative thereof, such as an acid halide, an acid anhydride, an activated ester, an activated amide or the like. Further, the reaction is preferably conducted by activating the amino radical of the starting compounds (II) and (IV) in the form of the reactive derivative thereof, for example, a derivative formed by the reaction of the compound (II) or (IV) with a silyl compound, phosphorus trichloride or phosgene or the like.

PROCESS 3

The reaction is usually carried out under the reducing condition, for example, in the presence of a reducing agent (e.g., lithium borohydride, sodium borohydride, etc.). The reaction can be carried out in a solvent such as alcohol (e.g. ethanol, methanol, etc.) or aqueous alcohol, at room temperature and preferably under around neutral condition.

PROCESS 4

The reaction may be carried out in a solvent such as water, acetone, chloroform, nitrobenzene, dimethylformamide, methanol, ethanol, dimethylsulfoxide or the like. The reaction is usually carried out at room temperature or slightly elevated temperature and preferably under around neutral condition.

This reaction is preferably carried out by using a salt of the compound (VIII) such as an alkali metal salt (e.g., sodium salt, potassium salt, etc.) or the like. When the compound (VIII) is used in a free form, the reaction is preferably conducted in the presence of a base.

PROCESS 5

The reaction is carried out in a solvent such as methylene chloride, acetone or the like, usually under cooling or at room temperature.

This reaction is preferably carried out by using a salt of the 1-(lower)alkylpiperazine such as an inorganic salt (e.g., hydrochloride etc.) and an organic salt (e.g., formate, acetate, etc.).

When 1-(lower)alkylpiperazine is used in a free form, the reaction may be preferably carried out by using the excess of the 1-(lower)alkylpiperazine or in the presence of a base.

With regard to the compound (I) prepared according to the processes as described above, the compound (I) wherein $R^5$ is heterocyclic-thio substituted with amino(-lower)alkyl may be acylated with an acylating agent in a conventional manner as described above to give a compound (I) wherein $R^5$ is heterocyclic-thio substituted with acylamino(lower)alkyl.

Further, the compound (I) wherein $R^5$ is heterocyclic-thio substituted with lower alkoxycarbonyl(lower)alkanesulfonamido(lower)alkyl may be hydrolyzed in a conventional manner, for example, in the presence of an organic or inorganic acid, or, organic or inorganic base to give a compound (I) wherein $R^5$ is heterocyclic-thio substituted with carboxy(lower)alkanesulfonamido(lower)alkyl.

Furthermore, it is to be noted that the compound (I) having protected amino and/or carboxy group in its molecule may be converted into the corresponding compound having free amino and/or carboxy group by conventional manner, if desired.

Lastly, the starting compound (III) to be used in the Process 1 can be prepared by reacting a 2-phenylglycine derivative with a corresponding carboxylic acid, sulfonic acid or aldehyde by conventional method as illustrated in the following scheme.

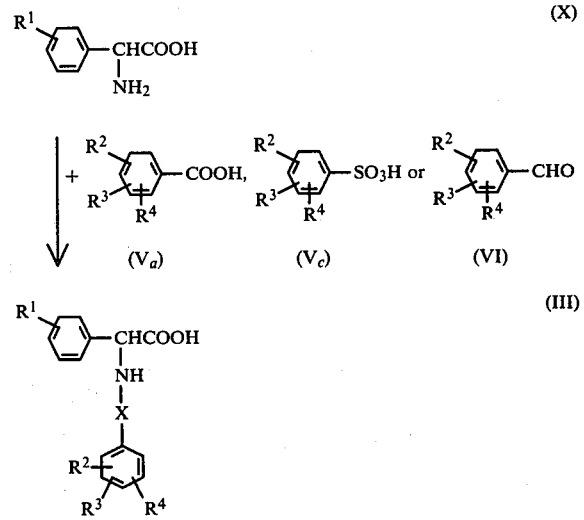

wherein $R^1$, $R^2$, $R^3$, $R^4$ and X are each as defined in the definition (i).

The object compounds (I) of the present invention exhibit high antibacterial activity and inhibit the growth of a number of microorganisms including Gram-positive and Gram-negative bacteria, especially Pseudomonus species. For therapeutic administration, the cephalosporin compounds (I) according to the present invention are used in the form of pharmaceutical preparation which contain said compound in admixture with pharmaceutically acceptable carriers such as an organic or inorganic solid or liquid excipient suitable for oral, parenteral or external administration. The pharmaceutical preparations may be in solid form such as capsules, tablets, dragees, ointments or suppositories, or in liquid form such as solutions, suspensions, or emulsions. If desired, there may be included in the above preparations auxiliary substances, stabilizing agents, wetting or emulsifying agents, buffers and other commonly used additives.

While the dosage of the compounds (I) will vary from and also depend upon the age and condition of the patient, an average single dose of about 50 mg., 100 mg., 250 mg., and 500 mg. of the compounds according to the present invention has proved to be effective in treating diseases caused by bacterial infection. In general amounts between 1 mg. and about 1000 mg. or even more may be administered.

Now, in order to show the utility of the object compounds, test data on anti-microbial activity of some representative compounds of the present invention are shown below.

TEST METHOD

In vitro activity against Pseudomonus aeruginosa NCTC-10490 was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu$g/ml. after incubation at 37° C. for 20 hours.

TEST RESULTS

| No. of the Examples | MIC ($\mu$g/ml.) |
|---|---|
| 1 | 1.56 |
| 2 | 0.78 |
| 3 | 0.78 |
| 4 | 0.78 |
| 5 | 0.78 |
| 6 | 1.56 |
| 7 | 0.78 |
| 8 | 0.78 |
| 9 | 1.56 |
| 25 | 1.56 |
| 52 | 1.56 |
| 53 | 1.56 |
| 56 | 12.5 |
| 63 | 6.25 |
| 67 | 1.56 |
| 69 | 6.25 |

The following examples are given for the purpose of illustrating the present invention:

EXAMPLE 1

7-(D-2-phenylglycinamido)-3-(1-methyl-1H-tetrazol-5-ylthiomethyl)-3-cephem-4-carboxylic acid (1.844 g.) and bis(trimethylsilyl)acetamide (3.2 g.) were added to methylene chloride (40 ml.). To the solution was added dropwise a solution of containing 2-hydroxy-5-chlorobenzoyl chloride (1.0 g.) in methylene chloriede (10 ml.) at 0° to 5° C. and the solution was stirred at the same temperature for an hour and additionally at room temperature for 30 minutes. After the solvent was distilled off under reduced pressure, ethyl acetate and water was added to the residue and the solution was acidified with 10% hydrochloric acid. The ethyl acetate layer was separated and extracted with an aqueous solution of sodium bicarbonate. Ethyl acetate was added on the aqueous extract and acidified with 10% hydrochloric acid. The ethyl acetate layer was separated, washed with water and a saturated aqueous solution of sodium chloride, dried over magnesium sulfate and concentrated under reduced pressure. The residue was treated with diethyl ether to give 7-[D-N-(2-hydroxy-5-chlorobenzoyl)-2-phenylglycinamido]-3-(1-methyl-1H-tetrazol-5-ylthiomehyl)-3-cephem-4-carboxylic acid (1.7 g.). M.p. 116° to 118° C. (dec.).

N.M.R.: $\delta(CD_3)_2CO+D_2O_{(ppm)}$: 3.7 (2H, s), 3.98 (3H, s), 4.38 (2H, s), 5.1 (1H, d, J=5 Hz), 5.83 (1H, d, J=5 Hz), 6.02 (1H, s), 6.93 (1H, d, J=9 Hz), 7.28–7.75 (6H, m), 8.03 (1H, d, J=3 Hz).

EXAMPLE 2

To the mixture of 7-(D-2-phenylglycinamido)-3-(1-methyl-1H-tetrazol-5-ylthiomethyl)-3-cephem-4-carboxylic acid (7.5 g.), methylene chloride (300 ml.) and bis(trimethylsilyl)acetamide (15 ml.) was added dropwise a solution of 2-hydroxy-3,5-dichlorobenzoylchloride (4.0 g.) in dry methylene chloride (50 ml.) under ice-cooling and the solution was stirred at the same temperature for 2 hours. The resultant solution was treated in a similar manner to that of Example 1 to give 7-[D-N-(2-hydroxy-3,5-dichlorobenzoyl)-2-phenylglycinamido]-3-(1-methyl-1H-tetrazol-5-ylthiomethyl)-3-cephem-4-carboxylic acid (5.4 g.). The ethereal washings were concentrated under reduced pressure. Petroleum ether was added to the residue and the precipitates were collected by filtration to give the same object compound (1.6 g.). Total yield (7.0 g.). The product was purified by dissolving in acetone and treated with activated charcoal. M.p. 180° to 185° C. (dec.).

N.M.R.: $\delta DMSO-d_{6(ppm)}$: 3.65 (2H, s), 3.95 (3H, s), 4.30 (2H, s), 5.10 (1H, s, J=4 Hz), 5.8–6.1 (2H, m), 7.3–7.6 (5H, m), 7.75 (1H, d, J=3 Hz), 8.22 (1H, d, J=3 Hz).

Thus obtained 7-[D-N-(2-hydroxy-3,5-dichlorobenzoyl)-2-phenylglycinamido]-3-(1-methyl-1H-tetrazol-5-ylthiomethyl)-3-cephem-4-carboxylic acid (1.5 g.) was suspended in water (30 ml.) and the suspension was stirred under ice-cooling. To the suspension was added a solution of L-arginine (723 mg.) in water (10 ml.), and stirred under ice-cooling for 10 minutes and additionally at room temperature for 20 minutes. The insoluble substance was filtered off and the filtrate was lyophilized to give L-arginine salt of 7-[D-N-(2-hydroxy-3,5-dichlorobenzoyl)-2-phenylglycinamido]-3-(1-methyl-1H-tetrazol-5-ylthiomethyl)-3-cephem-4-carboxylic acid (2.16 g.).

I.R.: $\nu_{max}^{Nujol*}$ (cm$^{-1}$): 1760, 1620 (broad).

EXAMPLE 3

To the mixture of 7-(D-2-phenylglycinamido)-3-(1-methyl-1H-tetrazol-5-ylthiomethyl)-3-cephem-4-carboxylic acid (2.5 g.), methylene chloride (150 ml.) and bis(trimethylsilyl)acetamide (5 ml.) was added dropwise a dry acetone solution (20 ml.) containing 2-hydroxy-5-nitrobenzoyl chloride, which was prepared by conventional manner from 2-hydroxy-5-nitrobenzoic acid (1.5 g.), with stirring under ice-cooling over 30 minutes. The mixture was stirred under ice-cooling for an hour and additionally at room temperature for an hour. The resultant solution was treated in a similar manner to that of Example 1 to give 7-[D-N-(2-hydroxy-5-nitrobenzoyl)-2-phenylglycinamido]-3-(1-methyl-1H-tetrazol-5-ylthiomethyl)-3-cephem-4-carboxylic acid (2.0 g.). The product was purified by dissolving in acetone and subjecting to column chromatography on silica gel. M.p. 150° to 155° C. (dec.).

N.M.R.: $\delta DMSO-d_{6(ppm)}$: 3.65 (2H, s), 3.95 (3H, s), 4.30 (2H, s), 5.05 (1H, d, J=5 Hz), 5.65–6.00 (2H, m), 7.15 (1H, d, J=9 Hz), 7.2–7.6 (5H, m), 8.25 (1H, dd, J=3 Hz, 9 Hz), 8.85 (1H, d, J=3 Hz).

EXAMPLE 4

2-Hydroxy-5-sulfamoylbenzoic acid (1.1 g.) and triethylamine (500 mg.) were added to methylene chloride (40 ml.), and the solution was stirred at room temperature for 30 minutes. To the solution was added dropwise a solution of thionyl chloride (600 mg.) in methylene chloride (10 ml.) with stirring under ice-cooling and stirred at the same temperature for an hour and additionally at room temperature for 30 minutes. The solution was added dropwise to the mixture of 7-(D-2-phenylglycinamido)-3-(1-methyl-1H-tetrazol-5-ylthiomethyl)-3-cephem-4-carboxylic acid (2.5 g.), methylene chloride (100 ml.) and bis(trimethylsilyl)acetamide (5 ml.) with stirring under ice-cooling, and the mixture was stirred at the same temperature for an hour. The resultant solution was treated in a similar manner to that of Example 1 to give 7-[D-N-(2-hydroxy-5-sulfamoylbenzoyl)-2-phenylglycinamido]-3-(1-methyl-1H-tetrazol-5-ylthiomethyl)-3-cephem-4-carboxylic acid (1.2 g.). The product was purified in a similar manner to that of Example 2. M.p. 180° to 185° C. (dec.).

N.M.R.: $\delta DMSO-d_{6(ppm)}$: 3.65 (2H, s), 3.95 (3H, s), 4.35 (2H, s), 5.10 (1H, d, J=4 Hz), 5.70–6.05 (2H, m), 7.25 (1H, d, J=8 Hz), 7.2–7.6 (5H, m), 7.95 (1H, dd, J=2 Hz, J=8 Hz), 8.50 (1H, d, J=2 Hz).

EXAMPLE 5

2-Hydroxy-5-acetylbenzoic acid (1.26 g.) and triethylamine (707 mg.) were added to methylene chloride (30 ml.), and the solution was stirred at room temperature for 30 minutes. To the solution was added dropwise a solution of thionyl chloride (840 mg.) in methylene chloride with stirring under ice-cooling and the mixture was stirred at the same temperature for an hour. The solution was added dropwise to a mixture of 7-(D-2-phenylglycinamido)-3-(1-methyl-1H-tetrazol-5-ylthiomethyl)-3-cephem-4-carboxylic acid (2.5 g.), methylene chloride (100 ml.) and bis(trimethylsilyl)acetamide (5 ml.) with stirring under ice-cooling, and stirred at the same temperature for 1.5 hours. The resultant solution was treated in a similar manner to that of Example 1 to give 7-[D-N-(2-hydroxy-5-acetylbenzoyl)-2-phenylglycinamido]-3-(1-methyl-1H-tetrazol-5-ylthiomethyl)-3-cephem-4-carboxylic acid (2.2 g.). The product was purified in a similar manner to that of Example 2. M.p. 180° to 185° C. (dec.).

N.M.R.: $\delta DMSO-d_{6(ppm)}$: 2.55 (3H, s), 3.64 (2H, s), 3.95 (3H, s), 4.25 (2H, s), 5.01 (1H, d, J=4 Hz), 5.60–5.90 (2H, m), 7.01 (1H, d, J=8 Hz), 7.2–7.5 (5H, m), 7.92 (1H, dd, J=2 Hz, 8 Hz), 8.50 (1H, d, J=2 Hz)

EXAMPLE 6

2-Hydroxy-4-chloro-5-cyanobenzoic acid (1.18 g.) and triethylamine (606 mg.) were added to methylene chloride (30 ml.), and the solution was stirred at room temperature for 30 minutes. To the solution was added dropwise a solution of thionyl chloride (1.44 g.) in methylene chloride (10 ml.) with stirring under ice-cooling, and the mixture was stirred at room temperature for 30 minutes and additionally at 40° C. for 1.5 hours and then evaporated under reduced pressure. The residue was dissolved in methylene chloride and the solution was added dropwise to a mixture of 7-(D-2-phenylglycinamido)-3-(1-methyl-1H-tetrazol-5-ylthiomethyl)-3-cephem-4-carboxylic acid (2.5 g.), methylene chloride (100 ml.) and bis(trimethylsilyl)acetamide (5 ml.) under ice-cooling and stirred at the same temperature for an hour. The solvent was distilled off under reduced pressure, and ethyl acetate and water were added to the residue. The ethyl acetate layer was separated and extracted with 5% aqueous solution of sodium bicarbonate. Ethyl acetate and 10% hydrochloric acid were added to the aqueous extract and the ethyl acetate layer was separated, washed with water and a saturated aqueous solution of sodium chloride in turn, dried over magnesium sulfate and then evaporated under reduced pressure. The residue was washed with diethyl ether to give 7-[D-N-(2-hydroxy-4-chloro-5-cyanobenzoyl)-2-phenylglycinamido]-3-(1-methyl-1H-tetrazol-5-ylthiomethyl)-3-cephem-4-carboxylic acid (2.1 g.). The product was purified by treating with activated charcoal and precipitating from a mixture of acetone and diethyl ether. M.p. 170° to 175° C. (dec.).

N.M.R.: $\delta$DMSO$-d_{6(ppm)}$: 3.64 (2H, s), 3.92 (3H, s), 4.25 (2H, s), 5.05 (1H, d, J=5 Hz), 5.65–5.95 (2H, m), 7.25 (1H, s), 7.2–7.6 (5H, m), 8.45 (1H, s).

EXAMPLE 7

To a mixture of 7-(D-2-phenylglycinamido)-3-(1-methyl-1H-tetrazol-5-ylthiomethyl)-3-cephem-4-carboxylic acid (3.0 g.), methylene chloride (150 ml.) and bis(trimethylsilyl)acetamide (6 ml.) was added dropwise a suspension of 2-hydroxy-4-chloro-5-carbamoylbenzoyl chloride (1.35 g.) in dry acetone (10 ml.) under ice-cooling. The solution was stirred at the same temperature for 30 minutes and further at room temperature for an hour. The resultant solution was treated in a similar manner to that of Example 6 to give 7-[D-N-(2-hydroxy-4-chloro-5-carbamoylbenzoyl)-2-phenylglycinamido]-3-(1-methyl-1H-tetrazol-5-ylthiomethyl)-3-cephem-4-carboxylic acid (1.8 g.). The product was purified in a similar manner to that of Example 6. M.p. 175° to 180° C. (dec.).

N.M.R.: $\delta$DMSO$-d_{6(ppm)}$: 3.55 (2H, s), 3.85 (3H, s), 4.25 (2H, s), 4.95 (1H, d, J=5 Hz), 5.60–5.90 (2H, m), 6.95 (1H, s), 7.1–7.4 (5H, m), 8.02 (1H, s)

EXAMPLE 8

2-Hydroxy-4-chloro-5-sulfamoylbenzoic acid (1.0 g.) and triethylamine (404 mg.) were added to methylene chloride (40 ml.) and stirred at room temperature for 10 minutes. To the solution was added a solution of thionyl chloride (480 mg.) in methylene chloride (5 ml.) with stirring under ice-cooling, and the solution was stirred at the same temperature for 30 minutes. The solution was added dropwise to a mixture of 7-(D-2-phenylglycinamido)-3-(1-methyl-1H-tetrazol-5-ylthiomethyl)-3-cephem-4-carboxylic acid (2.25 g.), methylene chloride (100 ml.) and bis(trimethylsilyl)acetamide (4.5 ml.) with stirring under ice-cooling, and the mixture was stirred at the same temperature for an hour. The resultant solution was treated in a similar manner to that of Example 1 to give 7-[D-N-(2-hydroxy-4-chloro-5-sulfamoylbenzoyl)-2-phenylglycinamido]-3-(1-methyl-1H-tetrazol-5-ylthiomethyl)-3-cephem-4-carboxylic acid (1.30 g.). The product was purified in a similar manner to that of Example 6. M.p. 179° to 182° C. (dec.)

N.M.R.: $\delta$DMSO$-d_{6(ppm)}$: 3.65 (2H, s), 3.95 (3H, s), 4.25 (2H, s), 5.05 (1H, d, J=4 Hz), 5.65–5.95 (2H, m), 7.20 (1H, s), 7.3–7.6 (5H, m), 8.55 (1H, s).

EXAMPLE 9

To a mixture of 7-(D-2-phenylglycinamido)-3-(1-methyl-1H-tetrazol-5-ylthiomethyl)-3-cephem-4-carboxylic acid (2.5 g.), methylene chloride (150 ml.) and bis(trimethylsilyl)acetamide (5 ml.) was added dropwise a solution of 2-hydroxy-3,5-dinitrobenzoyl chloride (1.5 g.) in methylene chloride (20 ml.) with stirring, under ice-cooling over 20 minutes, and the solution was stirred at the same temperature for 1.5 hours. After distilling off the solvent under reduced pressure, ethyl acetate, water and 10% hydrochloric acid (0.5 ml.) were added to the residue, and the ethyl acetate layer was separated and extracted with 5% aqueous solution of sodium bicarbonate. Ethyl acetate was added to the aqueous extract and adjusted to pH 1 to 2 with 10% hydrochloric acid. The ethyl acetate layer was separated, washed with a saturated aqueous solution of sodium chloride, dried over magnesium sulfate and then evaporated under reduced pressure. The residue was dissolved in a small amount of acetone and reprecipitated with diethyl ether to give 7-[D-N-(2-hydroxy-3,5-dinitrobenzoyl)-2-phenylglycinamido]-3-(1-methyl-1H-tetrazol-5-ylthiomethyl)-3-cephem-4-carboxylic acid (2.6 g.). The product was purified in a similar manner to that of Example 6. M.p. 173° to 175° C. (dec.).

N.M.R.: $\delta$(CD$_3$)$_2$CO$_{(ppm)}$: 3.65 (2H, s), 3.97 (3H, s), 4.38 (2H, s), 4.96 (1H, d, J=4 Hz), 5.7–6.2 (2H, m), 7.2–7.8 (5H, m), 8.75 (1H, d, J=4 Hz), 9.00 (1H, d, J=4 Hz).

EXAMPLE 10

2.5-Dihydroxybenzoic acid (1.84 g.) and triethylamine (1.21 g.) were added to methylene chloride (50 ml.) and stirred at room temperature for 15 minutes. To the solution was added dropwise a solution of thionyl chloride (1.43 g.) in methylene chloride with stirring under ice-cooling and the solution was stirred at the same temperature for 30 minutes. The solution was added dropwise to a mixture of 7-(D-2-phenylglycinamido)-3-(1-methyl-1H-tetrazol-5-ylthiomethyl)-3-cephem-4-carboxylic acid (2.5 g.), bis(trimethylsilyl)acetamide (8 ml.) and methylene chloride (120 ml.) with stirring under ice-cooling and then stirred at the same temperature for an hour. The resultant solution was treated in a similar manner to that of Example 1 to give 7-[D-N-(2,5-dihydroxybenzoyl)-2-phenylglycinamido]-3-(1-methyl-1H-tetrazol-5-ylthiomethyl)-3-cephem-4-carboxylic acid (1.5 g.). The product was purified in a similar manner to that of Example 2. M.p. 150° to 160° C. (dec.).

N.M.R.: $\delta$DMSO$-d_6$ $_{(ppm)}$: 3.62 (2H, s), 3.95 (3H, s), 4.28 (2H, s), 5.02 (1H, d, J=5 Hz), 5.65–5.95 (2H, m), 6.80 (2H, s), 7.2–7.6 (6H, m).

EXAMPLE 11

2-Hydroxy-5-methylsulfamoylbenzoic acid (1.38 g.) and triethylamine (606 mg.) were added to methylene chloride (40 ml.) and stirred at room temperature for an hour. To the solution was added dropwise a solution of thionyl chloride (720 mg.) in methylene chloride (10 ml.) with stirring under ice-cooling and the solution was stirred at the same temperature for 30 minutes. The solution was added dropwise to a mixture of 7-(D-2-phenylglycinamido)-3-(1-methyl-1H-tetrazol-5-ylthiomethyl)-3-cephem-4-carboxylic acid (2.5 g.), methylene chloride (100 ml.) and bis(trimethylsilyl)acetamide (5 ml.) with stirring under ice-cooling over 15 minutes, and stirred at the same temperature for 1.5 hours. The resultant solution was treated in s similar manner to that of Example 1 to give 7-[D-N-(2-hydroxy-5-methylsulfamoylbenzoyl)-2-phenylglycinamido]-3-(1-methyl-1H-tetrazol-5-ylthiomethyl)-3-cephem-4-carboxylic acid (1.5 g.). The product was purified by dissolving in acetone and treating with activated charcoal. M.p. 165° to 170° C. (dec.).

N.M.R.: $\delta$(CD$_3$)$_2$CO$_{(ppm)}$: 2.50 (3H, d), 3.65 (2H, s), 3.95 (3H, s), 4.35 (2H, s), 5.08 (1H, d, J=5 Hz), 5.70–6.05 (2H, m), 7.10 (1H, d, J=8 Hz), 7.3–7.7 (5H, m), 7.75 (1H, dd, J=3 Hz, 8 Hz), 8.35 (1H, d, J=3 Hz).

EXAMPLE 12

2-Hydroxy-5-phenylsulfamoylbenzoic acid (2.35 g.) and triethylamine (808 mg.) were added to methylene chloride (50 ml.). To the solution was added dropwise a solution of thionyl chloride (960 mg.) in methylene chloride (10 ml.) with stirring under ice-cooling. The solution was added dropwise to a mixture of 7-(D-2-phenylglycinamido)-3-(1-methyl-1H-tetrazol-5-ylthiomethyl)-3-cephem-4-carboxylic acid (2.5 g.), methylene chloride (120 ml.) and bis(trimethylsilyl)acetamide (7 ml.) with stirring under ice-cooling, and the mixture was stirred at the same temperature for 30 minutes and additionally at room temperature for an hour. The resultant solution was treated in a similar manner to that of Example 1 to give 7-[D-N-(2-hydroxy-5-phenylsulfamoylbenzoyl)-2-phenylglycinamido]-3-(1-methyl-1H-tetrazol-5-ylthiomethyl)-3-cephem-4-carboxylic acid (2.5 g.). The product was purified by washing with diethyl ether. M.p. 160° to 170° C. (dec.).

N.M.R.: $\delta(CD_3)_2CO_{(ppm)}$: 3.65 (2H, s), 3.90 (3H, s), 4.32 (2H, s), 5.05 (1H, d, J=4 Hz), 5.70–5.95 (2H, m), 6.90 (1H, d, J=9 Hz), 7.0–7.55 (10H, m), 7.72 (1H, dd, J=10 Hz, 3 Hz) 8.25 (1H, d, J=3 Hz).

EXAMPLE 13

2-Hydroxy-5-(N,N-diethylsulfamoyl)benzoic acid (1.9 g.) and triethylamine (707 mg.) were added to methylene chloride (50 ml.). To the solution was added dropwise a solution of thionyl chloride (840 mg.) in methylene chloride (10 ml.) with stirring under ice-cooling and stirred at the same temperature for 40 minutes. The solution was added dropwise to a mixture of 7-(D-2-phenylglycinamido)-3-(1-methyl-1H-tetrazol-5-ylthiomethyl)-3-cephem-4-carboxylic acid (2.5 g.), methylene chloride (120 ml.) and bis(trimethylsilyl)acetamide (7 ml.) with stirring under ice-cooling, and the mixture was stirred at the same temperature for an hour. The resultant solution was treated in a similar manner to that of Example 1 to give 7-[D-N-{2-hydroxy-5-(N,N-diethylsulfamoyl)benzoyl}-2-phenylglycinamido]-3-(1-methyl-1H-tetrazol-5-ylthiomethyl)-3-cephem-4-carboxylic acid (2.0 g.). The product was purified in a similar manner to that of Example 2. M.p. 140° to 150° C. (dec.).

N.M.R.: $\delta DMSO-d_{6(ppm)}$: 1.02 (6H, t, J=6 Hz), 3.12 (4H, q, J=6 Hz), 3.65 (2H, s), 3.95 (3H, s), 4.30 (2H, s), 5.05 (1H, d, J=4 Hz), 5.62–6.00 (2H, m), 7.15 (1H, d, J=9 Hz), 7.2–7.6 (5H, m), 7.80 (1H, dd, J=9 Hz, 2 Hz), 8.35 (1H, d, J=2 Hz).

EXAMPLE 14

A solution of 2-hydroxy-4-aminobenzoyl chloride (900 mg.) in methylene chloride (30 ml.) was added dropwise to a mixture of 7-(D-2-phenylglycinamido)-3-(5-methyl-1,3,4-thiadiazol-2-ylthiomethyl)-3-cephem-4-carboxylic acid (2.6 g.), methylene chloride (120 ml.) and bis(trimethylsilyl)acetamide (3.5 ml.) with stirring under ice-cooling over 5 minutes. The solution was stirred at the same temperature for an hour and further at room temperature for an hour. After distilling off the solvent under reduced pressure, ethyl acetate and water were added to the residue. The solution was acidified with 10% hydrochloric acid and the insoluble substance was filtered off. The ethyl acetate layer was separated, washed with water and a saturated aqueous solution of sodium chloride, dried over magnesium sulfate and then evaporated under reduced pressure. The residue was washed with diethyl ether to give 7-[D-N-(2-hydroxy-4-aminobenzoyl)-2-phenylglycinamido]-3-(5-methyl-1,3,4-thiadiazol-2-ylthiomethyl)-3-cephem-4-carboxylic acid (2.1 g.). The product was purified by dissolving in methanol, treating with activated charcoal, and then washing with diethyl ether. M.p. 170° to 180° C. (dec.).

N.M.R.: $\delta DMSO-d_{6(ppm)}$: 2.64 (3H, s), 3.55 (2H, s), 4.15, 4.55 (2H, $AB_q$, J=14 Hz), 4.95 (1H, d, J=5 Hz), 5.65–5.85 (2H, m), 5.9–6.1 (2H, m), 7.2–7.8 (6H, m).

EXAMPLE 15

A solution of salicyloyl chloride (1.17 g.) in methylene chloride (10 ml.) was added dropwise to a mixture of 7-(D-2-phenylglycinamido)-3-(5-methyl-1,3,4-thiadiazol-2-ylthiomethyl)-3-cephem-4-carboxylic acid (2.6 g.), methylene chloride (150 ml.) and bis(trimethylsilyl)acetamide (5.05 g.) with stirring at 0° C., and the mixture was stirred at the same temperature for an hour. The solvent was distilled off under reduced pressure and the residue was extracted with ethyl acetate. The extract was washed with a saturated aqueous solution of sodium chloride, dried over magnesium sulfate, and then evaporated under reduced pressure. The residue was washed with diethyl ether to give 7-(D-N-salicyloyl-2-phenylglycinamido)-3-(5-methyl-1,3,4-thiadiazol-2-ylthiomethyl)-3-cephem-4-carboxylic acid (2.4 g.). The product was dissolved in ethyl acetate, and the solution was filtered. The filtrate was subjected to column chromatography on silica gel and eluted with ethyl acetate. After distilling off the solvent under reduced pressure, the residue was washed with diethyl ether and petroleum ether in turn to give the pure product. M.p. 180° to 184° C. (dec.).

N.M.R.: $\delta DMSO-d_6$ $_{(ppm)}$: 2.65 (3H, s), 3.62 (2H, s) 4.20, 4.60 (2H, $AB_q$, J=14 Hz), 5.08 (1H, d, J=5 Hz), 5.7–6.0 (2H, m), 6.8–8.2 (9H, m)

EXAMPLE 16

2-Hydroxy-5-acetamidobenzoic acid (1.17 g.) and triethylamine (601 mg.) were added to methylene chloride (40 ml.) and stirred at room temperature for 30 minutes. To the solution was added dropwise a solution of thionyl chloride (714 mg.) in methylene chloride (10 ml.) under ice-cooling, and the solution was stirred at the same temperature for 25 minutes and additionally at room temperature for 15 minutes. The solution was added dropwise to a mixture of 7-(D-2-phenylglycinamido)-3-(5-methyl-1,3,4-thiadiazol-2-ylthiomethyl)-3-cephem-4-carboxylic acid (2.6 g.), methylene chloride (120 ml.) and bis(trimethylsilyl)acetamide (4.5 ml.) with stirring under ice-cooling over 20 minutes, and the mixture was stirred at the same temperature for 1.5 hours. The resultant solution was treated in a similar manner to that of Example 1 to give 7-[D-N-(2-hydroxy-5-acetamidobenzoyl)-2-phenylglycinamido]-3-(5-methyl-1,3,4-thiadiazol-2-ylthiomethyl)-3-cephem-4-carboxylic acid (1.3 g.). The product was dissolved in a small amount of acetone, and reprecipitated by adding diethyl ether to give the pure product. M.p. 180° to 187° C. (dec.).

N.M.R.: $\delta DMSO-d_{6(ppm)}$: 2.00 (3H, s), 2.72 (3H, s), 3.65 (2H, s), 4.20, 4.60 (2H, $AB_q$, J=14 Hz), 5.08 (1H, d, J=5 Hz), 5.65–6.00 (2H, m), 6.95 (1H, d, J=9 Hz), 7.3–7.6 (5H, m), 7.75 (1H, dd, J=3 Hz, 9 Hz), 8.08 (1H, d, J=3 Hz).

EXAMPLE 17

2-Hydroxy-5-sulfamoylbenzoic acid (1.3 g.) and triethylamine (601 mg.) were added to methylene chloride (40 ml.) and stirred at room temperature for 30 minutes. To the solution was added dropwise a solution of thionyl chloride (714 mg.) in methylene chloride (10 ml.) under ice-cooling, and stirred at the same temperature for an hour. The solution was added dropwise to a mixture of 7-(D-2-phenylglycinamido)-3-(5-methyl-1,3,4-thiadiazol-2-ylthiomethyl)-3-cephem-4-carboxylic acid (2.6 g.), methylene chloride (120 ml.) and bis(trimethylsilyl)acetamide (3.5 ml.) with stirring under ice-cooling, and the mixture was stirred at the same temperature for 1.5 hours. The resultant solution was treated in a similar manner to that of Example 1 to give 7-[D-N-(2-hydroxy-5-sulfamoylbenzoyl)-2-phenylglycinamido]-3-(5-methyl-1,3,4-thiadiazol-2-ylthiomethyl)-3-cephem-4-carboxylic acid (1.6 g.). The product was purified in a similar manner to that of Example 2. M.p. 185° to 192° C. (dec.).

N.M.R.: $\delta(CD_3)_2CO_{(ppm)}$: 2.72 (3H, s), 3.72 (2H, s), 4.22, 4.62 (2H, $AB_q$, J=14 Hz), 5.05 (1H, d, J=4 Hz), 5.80–6.15 (2H, m), 7.05 (1H, d, J=8 Hz), 7.2–7.7 (5H, m), 7.90 (1H, dd, J=2 Hz, 8 Hz), 8.42 (1H, d, J=2 Hz).

EXAMPLE 18

A solution of 2-hydroxy-5-chlorobenzoyl chloride (1.4 g.) in dry acetone (10 ml.) was added dropwise to a mixture of 7-(D-2-phenylglycinamido)-3-(5-methyl-1,3,4-thiadiazol-2-ylthiomethyl)-3-cephem-4-carboxylic acid (2.6 g.), methylene chloride (200 ml.) and bis(trimethylsilyl)acetamide (5.05 g.) with stirring at 0° C. over 10 minutes, and the mixture was stirred at the same temperature for an hour. The resultant solution was treated in a similar manner to that of Example 1 to give 7-[D-N-(2-hydroxy-5-chlorobenzoyl)-2-phenylglycinamido]3-(5-methyl-1,3,4-thiadiazol-2-ylthiomethyl)-3-cephem-4-carboxylic acid (2.1 g.). The product was dissolved in acetone, treated with activated charcoal and washed with diethyl ether and petroleum ether in turn to give the pure product. M.p. 175° to 179° C. (dec.).

N.M.R.: $\delta(CD_3)_2CO_{(ppm)}$: 2.65 (3H, s), 3.53, 3.83 (2H, $AB_q$, J=16 Hz), 4.22, 4.62 (2H, $AB_q$, J=14 Hz), 5.10 (1H, d, J=4 Hz), 5.75–6.05 (2H, m), 6.95 (1H, d, J=10 Hz), 7.2–7.7 (6H, m), 8.12 (1H, d, J=3 Hz).

EXAMPLE 19

A solution of 2-hydroxy-3,5-dichlorobenzoyl chloride (1.35 g.) in methylene chloride (10 ml.) was added dropwise to a mixture of 7-(D-2-phenylglycinamido)-cephalosporanic acid (2.0 g.), methylene chloride (50 ml.) and bis(trimethylsilyl)acetamide (5 ml.) over 5 minutes. Thereafter, the solution was stirred under ice-cooling for 20 minutes and further at room temperature for 1.5 hours. After the resultant solution was concentrated under reduced pressure, ethyl acetate and 3 N-hydrochloric acid were added to the residue, and the ethyl acetate layer was separated, washed with water and extracted with 5% aqueous solution of sodium bicarbonate. Ethyl acetate was added to the aqueous extract and adjusted to pH 3 with hydrochloric acid. The ethyl acetate layer was separated, washed with water and treated with activated charcoal, and then evaporated. The residue was washed with benzene (30 ml.) to give pale yellow powder (2.0 g.) of 7-[D-N-(2-hydroxy-3,5-dichlorobenzoyl)-2-phenylglycinamido]cephalosporanic acid. M.p.>120° C. (dec.).

N.M.R.: $\delta DMSO-d_6-D_2O_{(ppm)}$: 2.95 (3H, s), 3.27–3.65 (2H, m), 4.53, 4.9 (2H, $AB_q$, J=13 Hz), 4.95 (1H, d, J=5 Hz), 5.65 (1H, d, J=5 Hz), 5.7 (1H, s), 7.1–7.7 (5H, m), 7.67 (1H, d, J=2 Hz), 8.12 (1H, d, J=2 Hz)

EXAMPLE 20

A solution of 2-hydroxy-5-chlorobenzoyl chloride (2.57 g.) in methylene chloride (10 ml.) was added dropwise to a mixture of 7-[D-2-(4-hydroxyphenyl)-glycinamido]-3-(1-methyl-1H-tetrazol-5-yl-thiomethyl)-3-cephem-4-carboxylic acid (2.7 g.), bis(trimethylsilyl)acetamide (4.6 g.) and methylene chloride (50 ml.) under ice-cooling, and stirred at the same temperature for 3 hours. The resultant solution was treated in a similar manner to that of Example 1 to give 7-[D-N-(2-hydroxy-5-chlorobenzoyl)-2-(4-hydroxyphenyl)-glycinamido]-3-(1-methyl-1H-tetrazol-5-ylthiomethyl)-3-cephem-4-carboxylic acid (2.5 g.). The product was dissolved in ethyl acetate and treated with activated charcoal to give the pure product.

N.M.R.: $\delta(CD_3)_2CO-D_2O_{(ppm)}$: 3.73 (2H, s), 3.98 (3H, s), 4.4 (2H, s), 5.1 (1H, d, J=5 Hz), 5.83 (1H, d, J=5 Hz), 5.9 (1H, s), 6.7–7.5 (6H, m), 8.0 (1H, d, J=3 Hz).

EXAMPLE 21

A mixture of 7-[D-2-(3-mesylaminophenyl)-glycinamido]-3-(1-methyl-1H-tetrazol-5-ylthiomethyl)-3-cephem-4-carboxylic acid (2.47 g.), methylene chloride (150 ml.) and bis(trimethylsylil)acetamide (5.05 g.) was stirred at 0° to 3° C. for 30 minutes. To the solution was added dropwise a solution of salicyloyl chloride (1.05 g.) in acetone (10 ml.) with stirring at 0° C., and the solution was stirred at the same temperature for an hour. After distilling off the solvent under reduced pressure, ethyl acetate (60 ml.) and water (20 ml.) were added to the residue. The insoluble substance was filtered out and the ethyl acetate layer was separated from the filtrate. The aqueous layer was extracted with ethyl acetate, and the extract was combined with the ethyl acetate layer obtained above washed with a saturated aqueous solution of sodium chloride, and then extracted with 5% aqueous solution of sodium bicarbonate. Ethyl acetate was added to the aqueous extract and adjusted to pH 1 to 2 with 10% hydrochloric acid. The ethyl acetate layer was separated, washed with a saturated aqueous solution of sodium chloride, dried over magnesium sulfate and then evaporated under reduced pressure. The residue was washed with diethyl ether to give 7-[D-N-salicyloyl-2-(3-mesylaminophenyl)-glycinamido]-3-(1-methyl-1H-tetrazol-5-ylthiomethyl)-3-cephem-4-carboxylic acid (2.0 g.). The product was dissolved in acetone and reprecipitated by adding diethyl ether. The appearing precipitates were dissolved in ethyl acetate and purified by subjecting to column chromatography on silica gel. M.p. 166° to 169° C. (dec.).

N.M.R.: $\delta(CD_3)_2CO-D_2O_{(ppm)}$: 3.1 (3H, s), 3.60, 3.80 (2H, $AB_q$, J=16 Hz), 4.07 (3H, s), 4.38 (2H, s), 5.12 (1H, d, J=5 Hz), 5.86 (1H, d, J=5 Hz), 5.95 (1H, s), 6.9–8.2 (8H, m).

EXAMPLE 22

To a mixture of 7-(D-2-phenylglycinamido)-3-(1-methyl-1H-tetrazol-5-ylthiomethyl)-3-cephem-4-carboxylic acid (507 mg.), methylene chloride (30 ml.) and bis(trimethylsilyl)acetamide (1 ml.) was added a solution of 2-hydroxy-5-chlorosulfonylbenzoyl chloride (239 mg.) in dry acetone (5 ml.) with stirring under ice-cooling, and the mixture was stirred at the same temperature for an hour. After distilling off the solvent under reduced pressure, ethyl acetate, water and 10% hydrochloric acid (3 drops) were added to the residue. The insoluble substance was filtered out, and the ethyl acetate layer was separated, washed with water and a saturated aqueous solution of sodium chloride, dried over magnesium sulfate and then evaporated under reduced pressure. Diethyl ether was added to the residue, stirred and pulverized. The precipitates were collected by filtration and washed with diethyl ether to give 7-[D-N-(2-hydroxy-5-chlorosulfonylbenzoyl)-2-phenylglycinamido]-3-(1-methyl-1H-tetrazol-5-ylthiomethyl)-3-cephem-4-carboxylic acid (380 mg.).

N.M.R.: $\delta(CD_3)_2CO-D_2O_{(ppm)}$: 3.7 (2H, broad s), 4.0 (3H, s), 4.35 (2H, s), 5.05 (1H, d, J=5.5 Hz), 5.85 (1H, d, J=5.5 Hz), 5.93 (1H, s), 7.25-8.7 (8H, m).

Thus obtained 7-[D-N-(2-hydroxy-5-chlorosulfonylbenzoyl)-2-phenylglycinamido]-3-(1-methyl-1H-tetrazol-5-ylthiomethyl)-3-cephem-4-carboxylic acid (1.8 g.) and sodium bicarbonate (840 mg.) were dissolved in water (50 ml.). Ethyl acetate was added to the solution, and adjusted to pH 3 with 10% hydrochloric acid and then the aqueous layer was separated. Butanol (20 ml.) was added to the aqueous solution, adjusted to pH 2 with 10% hydrochloric acid, and then the butanol layer was separated and washed with a saturated aqueous solution of sodium chloride.

A solution of sodium 2-ethylhexanoate in butanol was added to the solution, and the precipitates were collected by filtration and washed with diethyl ether to give disodium salt of 7-[D-N-(2-hydroxy-5-sulfobenzoyl)-2-phenylglycinamido]-3-(1-methyl-1H-tetrazol-5-ylthiomethyl)-3-cephem-4-carboxylic acid (1.25 g.). The product was purified by washing with butanol and acetone. M.p. 230° to 240° C. (dec.).

N.M.R.: $\delta CD_3OD-D_2O-DCl_{(ppm)}$: 3.65 (2H, s), 4.05 (3H, s), 4.30 (2H, s), 5.05 (1H, d, J=5 Hz), 5.75 (1H, d, J=5 Hz), 5.80 (1H, s), 7.15 (1H, d, J=9 Hz), 7.3-7.6 (5H, m), 7.85 (1H, dd, J=3 Hz, 9 Hz), 8.35 (1H, d, J=3 Hz).

EXAMPLE 23

To a mixture of 7-(D-2-phenylglycinamido)cephalosporanic acid (5.67 g.), methylene chloride (300 ml.) and bis(trimethylsilyl)acetamide (10 ml.) was added dropwise a solution of 2-hydroxy-5-chlorobenzoyl chloride (3.3 g.) in methylene chloride (50 ml.) with stirring under ice-cooling over 30 minutes, and the solution was stirred at the same temperature for 1.5 hours. The solvent was distilled off under reduced pressure and ethyl acetate, water and 10% hydrochloric acid (0.5 ml.) were added to the residue. The ethyl acetate layer was separated, and 5% aqueous solution of sodium bicarbonate was added to the ethyl acetate solution. The precipitates were collected by filtration, and ethyl acetate and water were added to the solid substance. The solution was adjusted to pH 2-3 with 10% hydrochloric acid, and the ethyl acetate layer was separated, washed with a saturated aqueous solution of sodium chloride, dried over magnesium sulfate and then evaporated under reduced pressure. The residue was washed with diethyl ether and benzene to give 7-[D-N-(2-hydroxy-5-chlorobenzoyl)-2-phenylglycinamido]cephalosporanic acid (4.0 g.). The aqueous layer was separated from the filtrate, from which the solid substance was filtered out in the above, adjusted to pH 2 to 3 with 10% hydrochloric acid and extracted with ethyl acetate. The extract was washed with a saturated aqueous solution of sodium chloride, dried over magnesium sulfate and then evaporated under reduced pressure. The residue was washed with diethyl ether and benzene respectively to give the same object compound (1.0 g.). Total yield 5.0 g.

N.M.R.: $\delta(CD_3)_2CO-D_2O_{(ppm)}$: 2.02 (3H, s), 3.35, 3.7 (2H, $AB_q$, J=18 Hz), 4.77, 5.15 (2H, $AB_q$, J=15 Hz), 5.1 (1H, d, J=5 Hz), 5.9 (1H, d, J=5 Hz), 6.0 (1H, s), 6.95-8.1 (8H, m).

EXAMPLE 24

A solution of 2-chloroacetoxy-4-chlorobenzoyl chloride (1.66 g.) in methylene chloride (20 ml.) was added dropwise to a mixture of 7-(D-2-phenylglycinamido)-3-(1-methyl-1H-tetrazol-5-ylthiomethyl)-3-cephem-4-carboxylic acid (2.5 g.), methylene chloride (100 ml.) and bis(trimethylsilyl)acetamide (5 ml.) with stirring under ice-cooling, and the mixture was stirred at the same temperature for 1.5 hours and further at room temperature for an hour. After distilling off the solvent under reduced pressure, ethyl acetate, water and 10% hydrochloric acid (3 drops) were added to the residue. The ethyl acetate layer was separated, extracted with 5% aqueous solution of sodium bicarbonate and then allowed to stand for an hour. Ethyl acetate was added to the solution and adjusted to pH 3 with 10% hydrochloric acid. The ethyl acetate layer was separated, washed with water and a saturated aqueous solution of sodium chloride, dried over magnesium sulfate and then evaporated. The residue was washed with diethyl ether to give 7-[D-N-(2-hydroxy-4-chlorobenzoyl)-2-phenylglycinamido]-3-(1-methyl-1H-tetrazol-5-ylthiomethyl)-3-cephem-4-carboxylic acid (1.4 g.). The product was purified by dissolving in acetone and treating with activated charcoal. M.p. 160°-165° C. (dec.).

N.M.R.: $\delta CD_3OD-D_2O_{(ppm)}$: 3.62 (2H, s), 3.95 (3H, s), 4.25 (2H, s), 4.98 (1H, d, J=4 Hz), 5.75 (1H, d, J=4 Hz), 5.78 (1H, s), 6.8-7.0 (2H, m), 7.3-7.6 (5H, m), 7.85 (1H, d, J=8 Hz).

EXAMPLE 25

7-(D-2-Phenylglycinamido)-3-(1-methyl-1H-tetrazol-5-ylthiomethyl)-3-cephem-4-carboxylic acid (3.0 g.) and bis(trimethylsilyl)acetamide (4.8 g.) were added to dry methylene chloride (100 ml.). To the solution was added dropwise a solution of 2,4-bis(chloroacetoxy)benzoyl chloride (1.80 g.) in methylene chloride (6 ml.) with stirring under ice-cooling, and the mixture was stirred at the same temperature for 1.5 hours. The solvent was distilled off under reduced pressure, and the residue was dissolved in ethyl acetate (300 ml.). The solution was washed with 5% hydrochloric acid and water in turn and dried over magnesium sulfate and then evaporated under reduced pressure. The residue was pulverized with diisopropyl ether to give powder (4.0 g.) containing 7-[D-N-{2,4-bis(chloroacetoxy)benzoyl}-2-phenylglycinamido]-3-(1-methyl-1H-tetrazol-5-ylthiomethyl)-3-cephem-4-carboxylic acid. The powder was dissolved in a solution of sodium bicarbonate (5.5 g.) in water (200 ml.), and stirred at room temperature for 3 hours. Ethyl acetate (300 ml.) was added to the aqueous solution, adjusted to about pH 2 with 10% hydrochloric acid, and the ethyl acetate layer was separated, washed with water, dried over magnesium sulfate and then evaporated under reduced pressure. The residue was pulverized with diisopropyl ether, collected by filtration and washed with water to give 7-[D-N-(2,4-dihydroxybenzoyl)-2-phenylglycinamido]-3-(1-methyl-1H-tetrazol-5-ylthiomethyl)-3-cephem-4-carboxylic acid (2.28 g.). M.p. 159° to 165° C. (dec.).

N.M.R.: $\delta(CD_3)_2CO-D_2O_{(ppm)}$: 3.67 (2H, s), 4.01 (3H, s), 4.32 (2H, s), 5.05 (1H, d, J=5 Hz), 5.82 (1H, d, J=5 Hz), 5.92 (1H, s), 6.35–6.65 (2H, m), 7.25–7.90 (6H, m).

EXAMPLE 26

7-(D-2-Phenylglycinamido)-3-(1-methyl-1H-tetrazol-5-ylthiomethyl)-3-cephem-4-carboxylic acid (2.5 g.) and bis(trimethylsilyl)acetamide (5 ml.) were added to methylene chloride (100 ml.). To the solution was added dropwise a solution of 2-chloroacetoxy-4-mesylaminobenzoyl chloride (2.0 g.) in dry acetone (5 ml.) and methylene chloride (15 ml.) with stirring under ice-cooling, and the mixture was stirred at the same temperature for an hour. The resultant solution was treated in a similar manner to that of Example 24 to give 7-[D-N-(2-hydroxy-4-mesylaminobenzoyl)-2-phenylglycinamido]-3-(1-methyl-1H-tetrazol-5-ylthiomethyl)-3-cephem-4-carboxylic acid (2.0 g.). The product was purified by treating with activated charcoal in acetone. M.p. 175° to 180° C. (dec.).

N.M.R.: $\delta DMSO-d_{6(ppm)}$: 3.10 (3H, s), 3.65 (2H, s), 3.98 (3H, s), 4.30 (2H, s), 5.08 (1H, d, J=4 Hz), 5.70–6.00 (2H, m), 6.8–7.0 (2H, m), 7.3–7.5 (5H, m), 8.02 (1H, d, J=8 Hz).

EXAMPLE 27

7-(D-2-Phenylglycinamido)-3-(1-methyl-1H-tetrazol-5-ylthiomethyl)-3-cephem-4-carboxylic acid (2.25 g.) and bis(trimethylsilyl)acetamide (4.5 ml.) were added to methylene chloride (100 ml.). To the solution was added dropwise a solution of 2-chloroacetoxy-4-acetamidobenzoyl chloride (1.2 g.) in dry acetone (5 ml.) with stirring under ice-cooling, and the mixture was stirred at the same temperature for 2 hours. The resultant solution was treated in a similar manner to that of Example 24 to give 7-[D-N-(2-hydroxy-4-acetamidobenzoyl)-2-phenylglycinamido]-3-(1-methyl-1H-tetrazol-5-ylthiomethyl)-3-cephem-4-carboxylic acid (1.5 g.). The product was purified by treating with activated charcoal in acetone. M.p. 175° to 180° C. (dec.).

N.M.R.: $\delta CD_3OD-DCl_{(ppm)}$: 2.25 (3H, s), 3.62 (2H, s), 3.95 (3H, s), 4.25 (2H, s), 5.00 (1H, d, J=4 Hz), 5.75 (1H, d, J=4 Hz), 5.80 (1H, s), 7.0–7.9 (8H, m).

EXAMPLE 28

7-(D-2-Phenylglycinamido)-3-(1-methyl-1H-tetrazol-5-ylthiomethyl)-3-cephem-4-carboxylic acid (2.5 g.) and bis(trimethylsilyl)acetamide (6 ml.) were added to methylene chloride (120 ml.). To the solution was added dropwise a solution of 2,6-bis(chloroacetoxy)-benzoyl chloride (2.3 g.) in methylene chloride (10 ml.) with stirring under ice-cooling, and the mixture was stirred at the same temperature for an hour and further at room temperature for 4 hours. The resultant solution was treated in a similar manner to that of Example 24 to give 7-[D-N-(2,6-dihydroxybenzoyl)-2-phenylglycinamido]-3-(1-methyl-1H-tetrazol-5-ylthiomethyl)-3-cephem-4-carboxylic acid (1.7 g.). This product was dissolved in 5% aqueous solution of sodium bicarbonate, adjusted to pH 5 with 2% hydrochloric acid and extracted with ethyl acetate. The extract was washed with 1% hydrochloric acid, water and a saturated aqueous solution of sodium chloride in turn, dried over magnesium sulfate and then evaporated under reduced pressure. The residue was pulverized with a mixture of diethyl ether and petroleum ether to give the pure product. M.p. 175° to 180° C. (dec.).

N.M.R.: $\delta CD_3OD_{(ppm)}$: 3.65 (2H, s), 3.95 (3H, s), 4.30 (2H, s), 4.98 (1H, d, J=5 Hz), 5.75 (1H, d, J=5 Hz), 5.75 (1H, s), 6.4 (2H, d, J=9 Hz), 7.1–7.7 (6H, m).

EXAMPLE 29

7-(D-2-Phenylglycinamido)-3-(1-methyl-1H-tetrazol-5-ylthiomethyl)-3-cephem-4-carboxylic acid (2.25 g.) and bis(trimethylsilyl)acetamide (4.5 ml.) were added to methylene chloride (100 ml.). To the solution was added dropwise a solution of 2-acetoxy-5-acetamidobenzoyl chloride (1.0 g.) in acetone (5 ml.) with stirring under ice-cooling, and the mixture was stirred at the same temperature for an hour. The solvent was distilled off under reduced pressure. Ethyl acetate and water were added to the residue and acidified with hydrochloric acid. The ethyl acetate layer was separated and extracted with 5% aqueous solution of sodium bicarbonate. Ethyl acetate was added to the extract, adjusted to pH 3 with 10% hydrochloric acid, and then the ethyl acetate layer was separated, washed with water and a saturated aqueous solution of sodium chloride in turn, dried over magnesium sulfate and then evaporated under reduced pressure. The residue was washed with diethyl ether to give 7-[D-N-(2-acetoxy-4-acetamidobenzoyl)-2-phenylglycinamido]-3-(1-methyl-1H-tetrazol-5-ylthiomethyl)-3-cephem-4-carboxylic acid (1.6 g.). The product was dissolved in acetone, treated with activated charcoal, concentrated to a volume of 5 ml. under reduced pressure, and a small portion of diethyl ether was added to the concentrate. The appearing oil was removed by decantation and the solution was concentrated to a volume of 3 ml. under reduced pressure. Diethyl ether was added to the concentrate, and the precipitates were collected by filtration to give the pure product. M.p. 167° to 172° C. (dec.).

N.M.R.: $\delta DMSO-d_{6(ppm)}$: 2.08 (3H, s), 2.21 (3H, s), 3.62 (2H, s), 3.98 (3H, s), 4.28 (2H, s), 5.05 (1H, d, J=5 Hz), 5.65–5.90 (2H, m), 7.3–7.9 (8H, m).

EXAMPLE 30

A solution of 2-nitro-5-chlorobenzoic acid (250 mg.) in thionyl chloride (3 ml.) was heated under reflux for 2.5 hours, and added to dry methylene chloride (2 ml.). The solution was added dropwise to a mixture of 7-(D-2-phenylglycinamido)-3-(1-methyl-1H-tetrazol-5-ylthiomethyl)-3-cephem-4-carboxylic acid (510 mg.), bis(trimethylsilyl)acetamide (800 mg.) and methylene chloride (20 ml.) with stirring at 0° to 5° C. over 5 minutes, and the mixture was stirred at the same temperature for 2 hours. The solvent was distilled off under reduced pressure, and 5% aqueous solution (25 ml.) of sodium bicarbonate was added to the residue. Ethyl acetate (70 ml.) was added to the solution, adjusted to pH 2 with 10% hydrochloric acid, and the ethyl acetate layer was separated. The aqueous layer was extracted with ethyl acetate, and the extract was combined with the ethyl acetate layer obtained above, washed with water and dried over magnesium sulfate and then evaporated under reduced pressure to give 7-[D-N-(2-nitro-5-chlorobenzoyl)-2-phenylglycinamido]-3-(1-methyl-1H- tetrazol-5-ylthiomethyl)-3-cephem-4-carboxylic acid (0.69 g.). The product was purified by washing the diethyl ether.

N.M.R.: $\delta(CD_3)_2CO-D_2O_{(ppm)}$: 3.67 (2H, s), 4.00 (3H, s), 4.37 (2H, s), 5.03 (1H, d, J=5 Hz), 5.83 (1H, d, J=5 Hz), 5.92 (1H, s), 7.2-8.3 (8H, m).

EXAMPLE 31

2-(Acetylthio)benzoic acid (1.37 g.) and triethylamine (700 mg.) were added to methylene chloride (40 ml.) and stirred at room temperature for 15 minutes. To the solution was added dropwise a solution of thionyl chloride (833 mg.) in methylene chloride (10 ml.) with stirring under ice-cooling, and the mixture was stirred at the same temperature for 30 minutes. The solution was added dropwise to a mixture of 7-(D-2-phenylglycinamido)-3-(1-methyl-1H-tetrazol-5-ylthiomethyl)-3-cephem-4-carboxylic acid (2.5 g.), bis(trimethylsilyl)acetamide (6 ml.) and methylene chloride (120 ml.) with stirring under ice-cooling, and the mixture was stirred at the same temperature for an hour. The resultant solution was treated in a similar manner to that of Example 29 to give 7-[D-N-(2-acetylthiobenzoyl)-2-phenyl-glycinamido]-3-(1-methyl-1H-tetrazol-5-ylthiomethyl)-3-cephem-4-carboxylic acid (1.9 g.). The product was purified by treating with activated charcoal in acetone. M.p. 145° to 155° C. (dec.).

N.M.R.: $\delta CD_3OD_{(ppm)}$: 2.25 (3H, s), 3.62 (2H, s), 3.95 (3H, s), 4.35 (2H, s), 4.95 (1H, d, J=4 Hz), 5.68 (1H, d, J=4 Hz), 5.85 (1H, s), 7.2-7.7 (9H, m).

EXAMPLE 32

A solution of 2-methoxybenzoyl chloride (1.2 g.) in methylene chloride (20 ml.) was added dropwise to a mixture of 7-(D-2-phenylglycinamido)-3-(1-methyl-1H-tetrazol-5-ylthiomethyl)-3-cephem-4-carboxylic acid (2.5 g.), bis(trimethylsilyl)acetamide (6 ml.) and methylene chloride (120 ml.) with stirring under ice-cooling over 10 minutes, and the mixture was stirred at the same temperature for an hour. The resultant solution was treated in a similar manner to that of Example 29 to give 7-[D-N-(2-methoxybenzoyl)-2-phenylglycinamido]-3-(1-methyl-1H-tetrazol-5-ylthiomethyl)-3-cephem-4-carboxylic acid (2.0 g.). The product was purified by treating with activated charcoal. M.p. 140° to 150° C. (dec.).

N.M.R.: $\delta DMSO-d_{6(ppm)}$: 3.58 (2H, s), 3.85 (3H, s), 3.95 (3H, s), 4.2 (2H, s), 4.95 (1H, d, J=5 Hz), 5.60-5.90 (2H, m), 6.8-7.9 (9H, m).

EXAMPLE 33

A solution of 2-chlorobenzoic acid (175 mg.) in thionyl chloride (2 ml.) was heated under reflux for 2.5 hours. After distilling off the thionyl chloride under reduced pressure, the residue was dissolved in methylene chloride (2 ml.). The solution was added dropwise to a mixture of 7-(D-2-phenylglycinamido)-3-(1-methyl-1H-tetrazol-5-ylthiomethyl)-3-cephem-4-carboxylic acid (510 mg.), bis(trimethylsilyl)acetamide (800 mg.) and methylene chloride (20 ml.) at 0° to 5° C. over 10 minutes, stirred at the same temperature for an hour and additionally at room temperature for 30 minutes. After distilling off the methylene chloride under reduced pressure, the residue was dissolved in 5% aqueous solution of sodium bicarbonate (20 ml.) and washed with ethyl acetate. Ethyl acetate (50 ml.) was added to the aqueous solution, adjusted to about pH 2 with 10% hydrochloric acid and then the ethyl acetate was separated. The aqueous layer was extracted with ethyl acetate (20 ml.) and the extract was combined with the ethyl acetate layer obtained above, washed with a saturated aqueous solution of sodium chloride, dried over magnesium sulfate and then evaporated under reduced pressure. The residue was pulverized with diethyl ether to give 7-[D-N-(2-chlorobenzoyl)-2-phenylglycinamido]-3-(1-methyl-1H-tetrazol-5-ylthiomethyl)-3-cephem-4-carboxylic acid (450 mg.).

N.M.R.: $\delta(CD_3)_2CO-D_2O_{(ppm)}$: 3.67 (2H, s), 4.05 (3H, s), 4.40 (2H, s), 5.08 (1H, d, J=5 Hz), 5.90 (1H, d, J=5 Hz), 6.02 (1H, s), 7.20-7.80 (9H, m).

EXAMPLE 34

A solution of 2-(methylthio)benzoic acid (1.00 g.) in thionyl chloride (10 ml.) was heated under reflux for an hour, and the thionyl chloride was distilled off under reduced pressure. The residue was dissolved in methylene choride added dropwise to a mixture of 7-(D-2-phenylglycinamido)-3-(1-methyl-1H-tetrazol-5-ylthiomethyl)-3-cephem-4-carboxylic acid (3.0 g.), bis(trimethylsilyl)acetamide (4.8 g.) and methylene chloride (60 ml.) at 0°-5° C. and stirred at the same temperature for 5 hours. The resultant solution was treated in a similar manner to that of Example 29 to give 7-[D-N-(2-methylthiobenzoy)-2-phenylglycinamido]-3-(1-methyl-1H-tetrazol-5-ylthiomethyl)-3-cephem-4-carboxylic acid (2.4 g.). The product was dissolved in acetone and precipitated with diethyl ether to give the pure compound.

N.M.R.: $\delta(CD_3)_2CO-D_2O_{(ppm)}$: 2.37 (3H, s), 3.67 (2H, s), 3.97 (3H, s), 4.33 (2H, s), 5.03 (1H, d, J=5 Hz), 5.77 (1H, d, J=5 Hz), 5.93 (1H, s), 7.22-7.73 (9H, m).

EXAMPLE 35

Phthalic anhydride (810 mg.) was added to a mixture of 7-[D-2-(3-mesylaminophenyl)glycinamido]-3-(1-methyl-1H-tetrazol-5-ylthiomethyl)-3-cephem-4-carboxylic acid (2.77 g.), sodium bicarbonate (1.26 g.), water (150 ml.) and acetone (150 ml.) under ice-cooling and stirred at the same temperature for an hour. Acetone was distilled off under reduced pressure, and the residue was washed with ethyl acetate. Ethyl acetate was added to the solution and adjusted to pH 1 to 2 with 10% hydrochloric acid, and the ethyl acetate layer was separated, washed with a saturated aqueous solution of sodium chloride, dried over magnesium sulfate and then concentrated under reduced pressure to a volume of 10 ml. Diethyl ether was added to the concentrate and stirred. The precipitates were collected by filtration to give 7-[D-N-(2-carboxybenzoyl)-2-(3-mesylaminophenyl)glycinamido]-3-(1-methyl-1H-tetrazol-5-ylthiomethyl)-3-cephem-4-carboxylic acid (2.4 g.). M.p. 155° to 158° C. (dec.).

N.M.R.: $\delta(CD_3)_2CO_{(ppm)}$: 2.94 (3H, s), 3.68 (2H, s), 3.96 (3H, s), 4.38 (2H, s), 5.04 (1H, d, J=5 Hz), 5.78 (1H, d, J=5 Hz), 5.95 (1H, s), 7.2-8.0 (8H, m).

EXAMPLE 36

2-Acetoxy-5-acetamidobenzoic acid (2.37 g.) and triethylamine (1.05 g.) were added to methylene chloride (40 ml.) and stirred at room temperature for 30 minutes. A solution of thionyl chloride (1.19 g.) in methylene chloride (20 ml.) was added dropwise to the solution at 0° C. and stirred at room temperature for 1.5 hours. The solution was added dropwise to a mixture of 7-(D-2-phenylglycinamido)-3-(5-methyl-1,3,4-thiadiazol-2-ylthiomethyl)-3-cephem-4-carboxylic acid (5.2 g.), bis(trimethylsilyl)acetamide (10 ml.) and methylene chloride (300 ml.) with stirring under ice-cooling over 20 minutes, and the mixture was stirred at the same temperature for 1.5 hours. After distilling off the solvent under reduced pressure, the residue was extracted with ethyl acetate. Diethyl ether was added to the extract and the precipitates were collected by filtration to give 7-[D-N-(2-acetoxy-5-acetamidobenzoyl)-2-phenylglycinamido]-3-(5-methyl-1,3,4-thiadiazol-2-ylthiomethyl)-3-cephem-4-carboxylic acid (3.5 g.). From the mother liquid, the same product (0.8 g.) was recovered. Total yield 4.3 g. This product was dissolved in acetone, precipitated by adding diethyl ether, collected by filtration dissolved in methanol and then treated with activated charcoal to give the pure product. M.p. 170° to 175° C. (dec.).

N.M.R.: $\delta CD_3OD_{(ppm)}$: 2.12 (3H, s), 2.18 (3H, s), 2.65 (3H, s), 3.6 (2H, s), 4.15, 4.55 (2H, $AB_q$, J=14 Hz), 4.98 (1H, d, J=5 Hz), 5.75 (1H, d, J=5 Hz), 5.80 (1H, s), 7.0-8.0 (8H, m).

EXAMPLE 37

2-Mesylaminobenzoyl chloride (1.1 g.) was added to a mixture of 7-(D-2-phenylglycinamido)-3-(5-methyl-1,3,4-thiadiazol-2-ylthiomethyl)-3-cephem-4-carboxylic acid (2.47 g.), bis(trimethylsilyl)acetamide (3.8 g.) and methylene chloride (45 ml.) at 0° to 5° C., and stirred at the same temperature for 2 hours and further at room temperature for 30 minutes. After distilling off the solvent under reduced pressure, the residue was dissolved in an aqueous solution of sodium bicarbonate. The solution was washed with ethyl acetate, and ethyl acetate was added to the solution. The solution was adjusted to pH 3 to 4 with 10% hydrochloric acid, and the ethyl acetate layer was separated, washed with water, dried over magnesium sulfate and then evaporated under reduced pressure. The residue was washed with diethyl ether to give 7-[D-N-(2-mesylaminobenzoyl)-2-phenylglycinamido]-3-(5-methyl-1,3,4-thiadiazol-2-ylthiomethyl)-3-cephem-4-carboxylic acid (2.65 g.).

N.M.R.: $\delta(CD_3)_2CO-D_2O_{(ppm)}$: 2.7 (3H, s), 3.0 (3H, s), 3.67 (2H, s), 4.62, 4.22 (2H, $AB_q$, J=14 Hz), 5.07 (1H, d, J=5 Hz), 5.83 (1H, d, J=5 Hz), 5.93 (1H, s), 7.0-8.0 (9H, m).

EXAMPLE 38

7-(D-2-Phenylglycinamido)-3-(1-methyl-1H-tetrazol-5-ylthiomethyl)-3-cephem-4-carboxylic acid (2.54 g.) and bis(trimethylsilyl)acetamide (4.0 g.) were added to methylene chloride (100 ml.) under ice-cooling, and stirred at the same temperature for 30 minutes. To the solution was added 2-hydroxy-3,5-dichlorobenzenesulfonyl chloride (1.38 g.) and stirred at room temperature overnight. After distilling off the methylene chloride under reduced pressure, the residue was extracted with 5% aqueous solution of sodium bicarbonate. The aqueous extract was adjusted to pH 4 to 5 with hydrochloric acid and extracted with ethyl acetate. The solvent was distilled off from the extract under reduced pressure and the residue was pulverized with diethyl ether to give 7-[D-N-(2-hydroxy-3,5-dichlorobenzenesulfonyl)-2-phenylglycinamido]-3-(1-methyl-1H-tetrazol-5-ylthiomethyl)-3-cephem-4-carboxylic acid (1.4 g.). After distilling off the solvent from the ethereal mother liqueur under reduced pressure, the residue was pulverized with diisopropyl ether to give the same product (0.62 g.). Total yield 2.02 g. The product was dissolved in acetone and treated with activated charcoal, and the solvent was distilled off under reduced pressure. The residue was pulverized with diethyl ether to give the pure product. M.p. 134° to 136° C. (dec.).

N.M.R.: $\delta(CD_3)_2CO-D_2O_{(ppm)}$: 3.7 (2H, broad s), 4.03 (3H, s), 4.4 (2H, broad s), 5.02 (1H, d, J=5 Hz), 5.4 (1H, s), 5.7 (1H, d, J=5 Hz), 7.1-7.9 (7H, m).

EXAMPLE 39

7-D-2-Phenylglycinamido-3-(1-methyl-1H-tetrazol-5-ylthiomethyl)-3-cephem-4-carboxylic acid (2.3 g.) and 2-chlorobenzaldehyde (4.2 g.) were added to methanol (100 ml.). To the solution were added 1 N aqueous solution of sodium hydroxide (5 ml.), water (10 ml.) and sodium borohydride (1.3 g.), and then the solution was adjusted to pH 7 with hydrochloric acid. Methanol was distilled off under reduced pressure, and an aqueous solution of sodium bicarbonate and diethyl ether were added to the residue. The aqueous layer was separated, adjusted to pH 4 with hydrochloric acid and extracted with ethyl acetate. The extract was washed with a saturated aqueous solution of sodium chloride and concentrated under reduced pressure. The residue was dissolved in methanol and ethyl acetate was added to the solution. The precipitates were collected by filtration to give 7-[D-N-(2-chlorobenzyl)-2-phenylglycinamido]-3-(1-methyl-1H-tetrazol-5-ylthiomethyl)-3-cephem-4-carboxylic acid (0.74 g.). M.p. 120° to 125° C. (dec.). After distilling off the solvent from the mother liqueur under reduced pressure, the residue was washed with ethyl acetate to give the same product (0.35 g.). Furthermore the insoluble substance after the extraction with ethyl acetate was collected by filtration, added to a mixture of butanol and water, and then adjusted to pH 2 with hydrochloric acid. The butanol layer was separated, washed with water and evaporated under reduced pressure. The residue was washed with diethyl ether to give the same product (0.51 g.). Total yield 1.6 g.

N.M.R.: $\delta(CD_3)_2CO-D_2O-DCl_{(ppm)}$: 3.6 (2H, m), 3.97 (3H, s), 4.25 (2H, s), 4.45 (2H, s), 5.0 (1H, d, J=5 Hz), 5.4 (1H, s), 5.87 (1H, d, J=5 Hz), 7.3-7.8 (9H, m).

EXAMPLE 40

Formate (2.54 g.) of 7-(D-2-phenylglycinamido)-3-(1-methyl-1H-tetrazol-5-ylthiomethyl)-3-cephem-4-carboxylic acid and 2-formylbenzoic acid (5.25 g.) were added to a mixture of methanol (100 ml.) and 1 N aqueous solution of sodium hydroxide (20 ml). Sodium borohydride (0.836 g.) was gradually added to the solution, and methanol was distilled off under reduced pressure. Ethyl acetate and water were added to the residue, adjusted to pH 2 with 10% hydrochloric acid, and the aqueous layer was separated and extracted with butanol. The butanol extract was washed with water and concentrated to a volume of 10 ml. under reduced pressure, and diethyl ether was added to the residue. The precipitates were collected by filtration to give 7-[D-N-(2-carboxybenzyl)-2-phenylglycinamido]-3-(1-methyl-1H-tetrazol-5-ylthiomethyl)-3-cephem-4-carboxylic acid (2.1 g.).

N.M.R.: $\delta(CD_3)_2CO-D_2O_{(ppm)}$: 3.65 (2H, m), 4.02 (3H, s), 4.35 (2H, m), 4.5 (2H, broad s), 5.05 (1H, d, J=5 Hz), 5.50 (1H, broad s), 5.73 (1H, d, J=5 Hz), 7.4-8.2 (9H, m).

EXAMPLE 41

7-(D-2-Phenylglycinamido)-3-(1-methyl-1H-tetrazol-5-ylthiomethyl)-3-cephem-4-carboxylic acid (2.3 g.) and 2-methoxybenzaldehyde (4.0 g.) were added to a mixture of methanol (100 ml.) and 1 N aqueous solution of sodium hydroxide (5 ml.), and then sodium borohydride (1.13 g.) was gradually added to the mixture. The solvent was distilled off under reduced pressure, and water and diethyl ether were added to the residue. The aqueous layer was separated, adjusted to pH 2 with 10% hydrochloric acid and extracted with butanol. The extract was washed with water and evaporated under reduced pressure. The residue was washed with diethyl ether to give 7-[D-N-(2-methoxybenzyl)-2-phenylglycinamido]-3-(1-methyl-1H-tetrazol-5-ylthiomethyl)-3-cephem-4-carboxylic acid (2.3 g.). M.p. 135° to 138° C. (dec.).

N.M.R.: $\delta(CD_3)_2CO-D_2O_{(ppm)}$: 3.63 (2H, broad s), 3.9 (3H, s), 4.0 (3H, s), 4.4 (4H, broad s), 5.03 (1H, d, J=5 Hz), 5.37 (1H, s), 5.7 (1H, d, J=5 Hz), 6.85–7.8 (9H, m).

EXAMPLE 42

Formate (2.0 g.) of 7-(D-2-phenylglycinamido)-3-(1-methyl-1H-tetrazol-5-ylthiomethyl)-3-cephem-4-carboxylic acid and 2,4-dichlorobenzaldehyde (6.3 g.) were added to methanol (80 ml.), and then sodium borohydride (1.35 g.) was gradually added to the solution. The mixture was adjusted to pH 6 with 10% hydrochloric acid, and the solvent was distilled off under reduced pressure. Water and butanol were added to the residue, adjusted to pH 4 with 10% hydrochloric acid, and the butanol layer was separated, washed with a saturated aqueous solution of sodium chloride, and then evaporated under reduced pressure. The residue was washed with diethyl ether to give 7-[D-N-(2,4-dichlorobenzyl)-2-phenylglycinamido]-3-(1-methyl-1H-tetrazol-5-ylthiomethyl)-3-cephem-4-carboxylic acid (1.8 g.). The product was dissolved in methanol and crystallized by adding ethyl acetate to give the pure product. M.p. 135° to 140° C. (dec.).

N.M.R.: $\delta CF_3COOH-D_2O_{(ppm)}$: 3.64 (2H, m), 4.04 (3H, s), 4.26, 4.46 (2H, $AB_q$, J=16 Hz), 4.44 (2H, s), 5.1 (1H, d, J=4 Hz), 5.36 (1H, s), 5.78 (1H, d, J=4 Hz), 7.4–7.8 (8H, m).

EXAMPLE 43

Formate (2.53 g.) of 7-(D-2-phenylglycinamido)-3-(i-methyl-1H-tetrazol-5-ylthiomethyl)-3-cephem-4-carboxylic acid and sodium 2-formylbenzenesulfonate (8.32 g.) were added to a mixture of methanol (100 ml.) and 1 N aqueous solution of sodium hydroxide (5 ml.). Sodium borohydride (1.5 g.) was gradually added to the mixture and adjusted to pH 6 with 10% hydrochloric acid. After the solvent was distilled off under reduced pressure, water (40 ml.) and butanol (70 ml.) were added to the residue and then adjusted to pH 1 with 10% hydrochloric acid. The butanol layer was separated and the aqueous layer was extracted with butanol. The butanol layer and the extract were combined together, washed with a saturated aqueous solution of sodium chloride and dried over magnesium sulfate. After adding sodium 2-ethylhexanoate (2.1 g.), the solution was stirred for 30 minutes. Dry diethyl ether (150 ml.) was added to the solution and the precipitates were collected by filtration to give sodium 7-[D-N-(2-sulfobenzyl)-2-phenylglycinamido]-3-(1-methyl-1H-tetrazol-5-ylthiomethyl)-3-cephem-4-carboxylate (3.1 g.). The product was dissolved in water (10 ml.), adjusted to pH 1 with 10% hydrochloric acid, and the precipitates were collected by filtration to give the free acid (1.5 g.) of the above object compound.

N.M.R.: $\delta D_2O-NaHCO_{3(ppm)}$: 3.2, 3.63 (2H, $AB_q$, J=17 Hz), 3.95 (3H, s), 4.05(2H, m), 4.3 (2H, s), 4.9 (1H, d, J=5 Hz), 5.05 (1H, s), 5.55 (1H, d, J=5 Hz), 7.4–7.6 (8H, m).

EXAMPLE 44

Formate (2.63 g.) of 7-(D-2-phenylglycinamido)-3-(5-methyl-1,3,4-thiadiazol-2-ylthiomethyl)-3-cephem-4-carboxylic acid and 2-hydroxybenzaldehyde (3.0 g.) were added to a mixture of water (75 ml.), methanol (75 ml.) and 1 N aqueous solution of sodium hydroxide (2.5 ml.) and stirred under ice-cooling. Sodium borohydride (0.4 g.) was gradually added to the mixture, and stirred for 30 minutes. The resultant solution was adjusted to about pH 4 with hydrochloric acid and methanol was distilled off under reduced pressure. The remaining solution was acidified with hydrochloric acid and shaken with ethyl acetate. The precipitates were collected by filtration and washed with ethyl acetate to give 7-[D-N-(2-hydroxybenzyl)-2-phenylglycinamido]-3-(5-methyl-1,3,4-thiadiazol-2-ylthiomethyl)-3-cephem-4-carboxylic acid (1.3 g.). The product was added to a mixture of 2-hydroxybenzaldehyde (5 ml.) and absolute methanol (40 ml.), and stirred at room temperature for 6 hours,, and the precipitates were collected by filtration and washed with methanol and diethyl ether in turn to give the pure product. M.p. 150.5° to 153° C. (dec.).

NMR: $\delta CF_3COOH-D_2O_{(ppm)}$: 2.97 (3H, s), 3.43, 3.73 (2H, $AB_q$, J=20 Hz), 4.33 (2H, s), 4.38, 4.65 (2H, $AB_q$, J=16 Hz), 5.1 (2H, m), 5.7 (1H, d, J=6 Hz), 6.9–7.95 (9H, m).

EXAMPLE 45

To a mixture of 7-(D-2-phenylglycinamido)-3-(1-methyl-1H-tetrazol-5-ylthiomethyl)-3-cephem-4-carboxylic acid formate (2.55 g.), methanol (100 ml.), 2-hydroxybenzaldehyde (2.44 g.), a solution (50 ml.) of sodium acetate (2.5 g.) in acetic acid and water (1:19), and 1 N-aqueous solution of sodium hydroxide (5 ml.) were added a solution of sodium borohydride and dimethylamine hydrochloride in dimethyl-formamide (11 ml.) and the mixture was stirred at room temperature for 6 hours. Methanol was distilled off under reduced pressure, and diethyl ether and water were added to the residue. The diethyl ether layer was separated out, and butanol was added to the remaining mixture and adjusted to pH 2 with hydrochloric acid. The butanol layer was separated, and concentrated under reduced pressure. Diethyl ether was added to the residue, and stirred for an hour. The precipitates were collected by filtration and washed with diethyl ether and chloroform respectively to give 7-[D-N-(2-hydroxybenzyl)-2-phenylglycinamido]-3-(1-methyl-1H-tetrazol-5-ylthiomethyl)-3-cephem-4-carboxylic acid (2.36 g.). The product was dissolved in methanol, treated with activated charcoal and filtered. Water was added to the filtrate and evaporated under reduced pressure. The precipitates were collected by filtration and washed with a small amount of water to give the pure product. M.p. 146.5° to 156° C. (dec.).

N.M.R.: $\delta(CD_3)_2CO-D_2O_{(ppm)}$: 3.55 (2H, m), 4.0 (3H, s), 4.3 (4H, broad s), 5.03 (1H, d, J=5 Hz), 5.33 (1H, s), 5.7 (1H, d, J=5 Hz), 6.7–7.8 (9H, m).

EXAMPLE 46

7-(D-2-Phenylglycinamido)-3-(1-methyl-1H-tetrazol-5-ylthiomethyl)-3-cephem-4-carboxylic acid (2.55 g.) and 2-hydroxy-5-chlorobenzaldehyde (3.87 g.) were treated in a similar manner to that of Example 45 to give 7-[D-N-(2-hydroxy-5-chlorobenzyl)-2-phenyl-glycinamido]-3-(1-methyl-1H-tetrazol-5-ylthiomethyl)-3-cephem-4-carboxylic acid (1.96 g.). The product was dissolved in methanol, treated with activated charcoal and filtered water and methanol were added to the filtrate and concentrated under reduced pressure, and the precipitates were collected by filtration and dried at 70° C. in vacuo for 6 hours to give the pure product. M.p. 152° to 162° C. (dec.).

N.M.R.: $\delta(CD_3)_2CO-D_2O_{(ppm)}$: 3.55 (2H, m), 4.0 (3H, s), 4.3 (4H, m), 5.05 (1H, d, J=5 Hz), 5.22 (1H, s), 5.75 (1H, d, J=5 Hz), 7.0–7.8 (8H, m).

EXAMPLE 47

Sodium borohydride (2.28 g.) was gradually added to a mixture of 7-[D-2-(3-mesylaminophenyl)-glycinamido]-3-methyl-3-cephem-4-carboxylic acid (4.64 g.), methanol (200 ml.), 2-hydroxybenzaldehyde (7.32 g.), sodium acetate (5 g.), acetic acid (5 ml.) and water (100 ml.). The mixture was stirred at room temperature for 2 hours, adjusted to about pH 5 with hydrochloric acid and concentrated under reduced pressure. Diethyl ether and water were added to the residue and the aqueous layer was separated, adjusted to pH 2 with hydrochloric acid and then extracted with butanol. After distilling off the solvent from the extract under reduced pressure, diethyl ether was added to the residue and stirred. The precipitates were collected by filtration and washed with diethyl ether to give 7-[D-N-(2-hydroxybenzyl)-2-(3-mesylaminophenyl)-glycinamido]-3-methyl-3-cephem-4-carboxylic acid (6.09 g.). The product was purified by washing with chloroform. M.p. 178° to 181° C. (dec.).

N.M.R.: $\delta(CD_3)_2CO-D_2O_{(ppm)}$: 2.05 (3H, s), 3.07 (3H, s), 3.15, 3.5 (2H, AB$_q$, J=18 Hz), 4.3 (2H, s), 5.03 (1H, d, J=5 Hz), 5.45 (1H, s), 5.65 (1H, d, J=5 Hz), 6.6–7.75 (9H, m).

EXAMPLE 48

A mixture of dimethylformamide (0.8 g.) and thionyl chloride (2.35 g.) was stirred at 50° C. for 30 minutes, and the excess of thionyl chloride was distilled off under reduced pressure. The residue was washed with diethyl ether, and diethyl ether (10 ml.) was added to the solution and concentrated under reduced pressure. Methylene chloride (80 ml.) and dimethylformamide (20 ml.) were added to the residue and further D-N-(2-chlorobenzoyl)glycine (3 g.) was added thereto at −20° C. The mixture was stirred at the same temperature for 30 minutes and then cooled to −40° C. A solution of 7-amino-3-(1-methyl-1H-tetrazol-5-ylthiomethyl)-3-cephem-4-carboxylic acid (3.28 g.), bis(trimethylsilyl)acetamide (10 g.) in methylene chloride (100 ml.), was cooled to −30° C., added to the above solution and then stirred at −20° C. for 1.5 hours. The solvent was distilled off under reduced pressure, and 5% aqueous solution of sodium bicarbonate was added to the residue and washed with ethyl acetate. Ethyl acetate was added to the solution and adjusted to pH 2 with 10% hydrochloric acid, and the ethyl acetate layer was separated. The aqueous layer was extracted with ethyl acetate twice, and the extracts were combined with the ethyl acetate layer, washed with water, dried over magnesium sulfate and then evaporated under reduced pressure. The residue was pulverized with diethyl ether to give pale yellow powder (1.8 g.) of 7-[D-N-(2-chlorobenzoyl)-2-phenylglycinamido]-3-(1-methyl-1H-tetrazol-5-ylthiomethyl)-3-cephem-4-carboxylic acid. The product was dissolved in a small amount of acetone, decolored, and reprecipitated with diethyl ether to give the pure product. This product was identified with the objective compound in Example 33 by N.M.R. spectrum.

EXAMPLE 49

7-[D-N-(2-Hydroxy-3,5-dichlorobenzoyl)-2-phenyl-glycinamido]cephalosporanic acid (5.9 g.), sodium bicarbonate (2.5 g.) and 5-aminomethyl-1,3,4-thiadiazol-2-thiol hydrochloride (2.0 g.) were added to a mixture of phosphate buffer (pH 5.2) (150 ml.) and acetone (75 ml., stirred at 65° C. for 7 hours and then allowed to stand for 3 days. The precipitates were collected by filtration and washed with acetone and diethyl ether to give 7-[D-N-(2-hydroxy-3,5-dichlorobenzoyl)-2-phenyl-glycinamido]-3-(5-aminomethyl-1,3,4-thiadiazol-2-ylthiomethyl)-3-cephem-4-carboxylic acid (2.3 g.). M.p. 205° to 210° C. (dec.).

N.M.R.: $\delta DMSO-d_6-D_2O_{(ppm)}$: 3.35–3.65 (2H, m), 4.2–4.4 (2H, m), 4.5 (2H, s), 4.63 (1H, d, J=5 Hz), 4.93 (1H, d, J=5 Hz), 4.77 (1H, s), 7.1–7.63 (5H, m), 7.5 (1H, d, J=4 Hz), 7.9 (1H, d, J=4 Hz).

EXAMPLE 50

A mixture of 85% phosphoric acid (20 g.) and phosphorus pentoxide (20 g.) was stirred at 120° C. for 3 hours. A mixture of thus obtained polyphosphoric acid (10 g.), sulfoacetic acid mono-hydrate (4.7 g.) and 5-amino-1,3,4-thiadiazole-2-thiol (1.3 g.) was stirred at 120° C. for 15 hours. After decomposing the polyphosphoric acid by adding ice-water, the mixture was subjected to column chromatography on nonionic absorption resin, "Amberite XAD-4" (Trademark: manufactured by Rohm and Haas Co.). Hydrochloric acid (pH 1) was passed through the column until phosphoric acid was not detected. Thereafter, water was passed through the column and the eluate was fractionated to each volume of 40 ml. The fractions from 10th to 35th were combined together and concentrated under reduced pressure. The pale brown residue was washed with acetone to give pale yellow solid (0.35 g.) of sodium N-(5-mercapto-1,3,4-thiadiazole-2-yl)carbamoylmethanesulfonate. On the other hand, the acetone washings was evaporated under reduced pressure and the residue was washed with diethyl ether, ethyl acetate and diethyl ether in turn to give the same product (0.38 g.). Total yield 0.73 g.

I.R.: $\nu_{max}^{Nujol*}$ (cm$^{-1}$): 1670.

The free sulfonic acid (0.68 g.) which was obtained from the sodium sulfonate by conventional manner, 7-[D-N-(2-hydroxy-3,5-dichlorobenzoyl)-2-phenyl-glycinamido]cephalosporanic acid (1.58 g.) and sodium bicarbonate (0.68 g.) were added to a mixture of phosphate buffer (pH 6.4) (60 ml.) and acetone (18 ml.), adjusted to pH 6.2 to 6.4 with 2 N hydrochloric acid, stirred at 63° to 65° C. for 11 hours, washed with ethyl acetate, adjusted to pH 1 to 2 with hydrochloric acid and then extracted with ethyl acetate. The extract was washed with water, dried over magnesium sulfate and concentrated under reduced pressure. The residue was pulverized with diethyl ether to give monosodium salt of 7-[D-N-(2-hydroxy-3,5-dichlorobenzoyl)-2-phenyl-glycinamido]-3-(5-sulfonatoacetamido-1,3,4-thiadiazol-2-ylthiomethyl)-3-cephem-4-carboxylic acid (0.6 g.).

N.M.R.: $\delta DMSO-d_6-D_2O_{(ppm)}$: 3.5, 3.7 (2H, AB$_q$, J=16 Hz), 3.74 (2H, s), 4.14, 4.4 (2H, AB$_q$, J=16 Hz), 5.05 (1H, d, J=6 Hz), 5.7 (1H, d, J=6 Hz), 5.76 (1H, s), 7.24–7.8 (5H, m), 7.7 (1H, d, J=2 Hz), 8.16 (1H, d, J=2 Hz).

EXAMPLE 51

To an aqueous solution (300 ml.) of 7-[D-N-(2-hydroxy-5-chlorobenzoyl)-2-phenylglycinamido]cephalosporanic acid (4.4 g.) and sodium bicarbonate (2.0 g.) was added 3-(5-mercapto-1,3,4-thiadiazol-2-ylcarbamoyl)propionic acid (1.9 g.), and stirred under heating for 4.5 hours. The solution was cooled, washed with ethyl acetate (100 ml.) twice, and adjusted to pH 2 with 10% hydrochloric acid. The precipitates were collected by filtration and washed with water and ethyl acetate in turn to give 7-[D-N-(2-hydroxy-5-chlorobenzoyl)-2-phenylglycinamido]-3-[5-(3-carboxypropionamido)-1,3,4-thiadiazol-2-ylthiomethyl]-3-cephem-4-carboxylic acid (2.8 g.).

N.M.R.: $\delta CD_3OD_{(ppm)}$: 2.75 (4H, s), 3.44, 3.64 (2H, $AB_q$, J=18 Hz), 4.10, 4.30 (2H, ABq, J=12 Hz), 4.92 (1H, d, J=5 Hz), 5.68 (1H, d, J=5 Hz), 5.75 (1H, s), 6.80 (1H, d, J=9 Hz), 7.1–7.5 (6H, m), 7.78 (1H, d, J=3 Hz).

EXAMPLE 52

A solution of 1-methylpiperazine (235 mg.) in methylene chloride (5 ml.) was added dropwise to a mixture of 7-[D-N-(2-hydroxy-5-chlorosulfonylbenzoyl)-2-phenylglycinamido]-3-(1-methyl-1H-tetrazol-5-ylthiomethyl)-3-cephem-4-carboxylic acid (1.6 g.), methylene chloride (50 ml.) and bis(trimethylsilyl)acetamide (2.5 ml.) with stirring under ice-cooling over 10 minutes, and the mixture was stirred at the same temperature for 1.5 hours. After distilling off the solvent under reduced pressure, ethyl acetate and water were added to the residue. The precipitates were collected by filtration and washed with ethyl acetate and water to give 7-[D-N-{2-hydroxy-5-(4-methyl-1-piperazinylsulfonyl)benzoyl}-2-phenylglycinamido]-3-(1-methyl-1H-tetrazol-5-ylthiomethyl)-3-cephem-4-carboxylic acid (1.6 g.). M.p. 190° to 195° C. (dec.).

N.M.R.: $\delta(CD_3)_2CO-DCl_{(ppm)}$: 3.08 (3H, s), 3.0–4.0 (8H, m), 3.75 (2H, s), 4.08 (3H, s), 4.42 (2H, s), 5.18 (1H, d, J=5 Hz), 5.90 (1H, d, J=5 Hz), 6.05 (1H, s), 7.4–7.8 (6H, m), 7.96 (1H, dd, J=8 Hz, 4 Hz), 8.50 (1H, d, J=4 Hz).

EXAMPLE 53

Bis(trimethylsilyl)acetamide (3.3 ml.) was added to a mixture of 7-[D-N-(2-hydroxy-3,5-dichlorobenzoyl)-2-phenylglycinamido]-3-(5-aminomethyl-1,3,4-thiadiazol-2-ylthiomethyl)-3-cephem-4-carboxylic acid (1.20 g.) and acetonitrile (40 ml.) with stirring under ice-cooling, and the mixture was stirred for 15 minutes. To the solution was added dropwise a solution of ethyl chlorosulfonyl acetate (0.38 g.) in acetonitrile (2 ml.) and stirred under ice-cooling for an hour. The solution was concentrated under reduced pressure, and ethyl acetate and water were added to the residue. The ethyl acetate layer was separated and the remaining aqueous layer was extracted with ethyl acetate. The ethyl acetate layer and the extract were combined together, washed with water, dried over magnesium sulfate, treated with activated charcoal and then evaporated under reduced pressure. The residue was pulverized with diethyl ether to give pale green powder (1.3 g.) of 7-[D-N-(2-hydroxy-3,5-dichlorobenzoyl)-2-phenylglycinamido]-3-(5-ethoxycarbonylmesylaminomethyl-1,3,4-thiadiazol-2-ylthiomethyl)-3-cephem-4-carboxylic acid.

N.M.R.: $\delta DMSO-d_6-D_2O_{(ppm)}$: 3.47–3.8 (2H, m), 4.3 (2H, s), 4.2–4.5 (2H, m), 4.67 (2H, s), 5.05 (1H, d, J=6.5 Hz), 5.77 (1H, d, J=6.5 Hz), 5.8 (1H, s), 7.2–7.65 (5H, m), 7.7 (1H, d, J=2 Hz), 8.2 (1H, d, J=2 Hz).

EXAMPLE 54

7-[D-N-(2-hydroxy-3,5-dichlorobenzoyl)-2-phenylglycinamido]-3-(5-ethoxycarbonylmesylaminomethyl-1,3,4-thiadiazol-2-ylthiomethyl)-3-cephem-4-carboxylic acid (1.1 g.) and sodium bicarbonate (0.34 g.) were added to water (20 ml.) and the solution was stirred at 50° C. for 10 hours, meanwhile sodium bicarbonate (each 0.1 g.) was added to the solution after stirring 3 hours and 5 hours, respectively. The resultant solution was adjusted to about pH 4 with 6 N-hydrochloric acid and extracted with ethyl acetate. The extract was dried over magnesium sulfate, treated with activated charcoal and then evaporated under reduced pressure. The residue was pulverized with diethyl ether to give 7-[D-N-(2-hydroxy-3,5-dichlorobenzoyl)-2-phenylglycinamido]-3-(5-carboxymesylaminomethyl-1,3,4-thiadiazol-2-ylthiomethyl)-3-cephem-4-carboxylic acid (0.35 g.). M.p. 164° to 172° C. (dec.).

N.M.R.: $\delta DMSO-d_6-D_2O_{(ppm)}$: 3.5–3.8 (2H, m), 4.23 (2H, s), 4.4–4.7 (2H, broad s), 4.65 (2H, s), 5.12 (1H, d, J=4 Hz), 5.8 (1H, d, J=4 Hz), 5.87 (1H, s), 7.3–7.65 (5H, m), 7.75 (1H, d, J=2 Hz), 8.2 (1H, d, J=2 Hz).

EXAMPLE 55

7-[D-N-(2-hydroxy-3,5-dichlorobenzoyl)-2-phenylglycinamido]-3-(5-aminomethyl-1,3,4-thiadiazol-2-ylthiomethyl)-3-cephem-4-carboxylic acid (1.02 g.) was added to a mixture of 5% aqueous solution of sodium bicarbonate (50 ml.) and acetone (20 ml.), and the solution was stirred under cooling with a mixture of salt and ice. Chlorosulfonylacetyl chloride (3 g.) was added dropwise to the solution at 5° to 10° C. over 50 minutes, meanwhile the solution was kept at pH 7 to 8 with 1 N aqueous solution of sodium hydroxide. After distilling off the acetone under reduced pressure, the residue was washed with ethyl acetate, treated with activated charcoal and filtered. Sodium chloride (10 g.) was dissolved in the filtrate, adjusted to pH 2 with 6 N hydrochloric acid and allowed to stand under cooling for an hour. The solution was centrifuged and the separated colloidal substance was collected by filtration with suction washed with water and dried in vacuo to give monosodium salt (0.9 g.) of 7-[D-N-(2-hydroxy-3,5-dichlorobenzoyl)-2-phenylglycinamido]-3-(5-sulfonatoactamidomethyl-1,3,4-thiadiazol-2-ylthiomethyl)-3-cephem-4-carboxylic acid. M.p. 179° to 190° C. (dec.).

N.M.R.: $\delta DMSO-d_6-D_2O_{(ppm)}$: 3.65 (2H, s), 3.5–3.75 (2H, broad s), 4.2–4.6 (2H, m), 4.8 (2H, s), 5.2 (1H, d, J=5 Hz), 5.85 (1H, d, J=5 Hz), 5.95 (1H, s), 7.45–7.75 (5H, m), 7.85 (1H, d, J=2 Hz), 8.25 (1H, d, J=2 Hz).

EXAMPLE 56

Formate (2.6 g.) of 7-(D-2-phenylglycinamido)-3-(5-methyl-1,3,4-thiadiazol-2-yl)thiomethyl-3-cephem-4-carboxylic acid was suspended in water (50 ml.) under ice-cooling, and the suspension was adjusted to pH 6.8 with 5% aqueous solution of sodium bicarbonate. To the suspension was added dropwise 2,5-dioxo-4-phenyl-1,3-dioxorane (1.07 g.) over 10 minutes, meanwhile the solution was kept at pH 6.6 to 6.8 with 5% aqueous solution of sodium bicarbonate. The solution was stirred under ice-cooling for an hour and adjusted to pH 1 with 10% hydrochloric acid. The precipitates were collected by filtration and washed with water to give 7-[D-N-(D-mandeloyl)-2-phenylglycinamido]-3-(5-methyl-1,3,4-thiadiazol-2-ylthiomethyl)-3-cephem-4-carboxylic acid (2.3 g.). Yield 75.6%. M.p. 135° to 138° C. (dec.).

I.R.: $\nu_{max}^{Nujol*}$ 1780 cm$^{-1}$.

N.M.R.: δAcetone−d$_6$+D$_2$O$_{(ppm)}$: 2.71 (3H, s), 3.46, 3.82 (2H, AB−$_q$, J=15 Hz), 4.05 (3H, s), 4.2, 4.55 (2H, AB−$_q$, J=14 Hz), 5.02 (1H, d, J=5 Hz), 5.2 (1H, s), 5.75 (1H, s), 5.8 (1H, d), 7.15–7.9 (10H, m).

EXAMPLE 57

Phosphorus pentachloride (1.04 g.) was added to a solution of 2-dichloroacetoxyimino-2-phenylacetic acid [syn isomer] (1.38 g.) in methylene chloride (25 ml.) under ice-cooling and stirred for 15 minutes. After distilling off the solvent under reduced pressure, methylene chloride (10 ml.) was added to the residue containing the acid chloride. The solution was added to a solution of formate (2.6 g.) of 7-(D-2-phenylglycinamido)-3-(5-methyl-1,3,4-thiadiazol-2-ylthiomethyl)-3-cephem-4-carboxylic acid and bis(trimethylsilyl)acetamide (4.0 g.) in methylene chloride (50 ml.) at −30° C., and the mixture was stirred at −25° to −30° C. for 2 hours and further at room temperature for 30 minutes. After distilling off the methylene chloride under reduced pressure, the residue was dissolved in an aqueous solution of sodium bicarbonate. The solution was shaken with ethyl acetate, and the aqueous layer was separated, adjusted to pH 3 to 4 with 10% hydrochloric acid and then extracted with ethyl acetate. The extract was washed with water, dried over magnesium sulfate, treated with activated charcoal and then concentrated under reduced pressure to give powder (1.4 g.) of 7-[D-N-(2-hydroxyimino-2-phenylacetyl)-2-phenylglycinamido]-3-(5-methyl-1,3,4-thiadiazol-2-ylthiomethyl)-3-cephem-4-carboxylic acid [syn-isomer]. Yield 45%. The product was recrystallized from a small amount of ethyl acetate to give the pure product (850 mg.). M.p. 130° to 133° C.

I.R.: $\nu_{max}^{Nujol*}$: 1770 cm$^{-1}$.

N.M.R.: δDMSO−d$_{6(ppm)}$: 2.84 (2H, s), 3.63 (2H, broad s), 4.25, 4.62 (2H, AB−q, J=14 Hz), 5.1 (1H, d, J=5 Hz), 5.7–6.02 (2H, m), 7.35–7.8 (10H, m).

EXAMPLE 58

To a suspension of 7-(D-2-phenylglycinamido)cephalosporanic acid (2.0 g.), sodium bicarbonate (1.2 g.) and water (40 ml.) was added dropwise a solution of triethylamine salt (2.3 g.) of ethyl (2-phenyl-2-sulfoacetoxy)formate in acetone (30 ml.) with stirring under ice-cooling over 5 minutes, and the mixture was stirred at the same temperature for an hour. After removing the insoluble substance by filtration, acetone was distilled off under reduced pressure. The residue was saturated with sodium chloride and extracted with n-butanol at pH 8, pH 3 and pH 1, successively. The extracts at pH 3 and pH 1 were dried over magnesium sulfate and concentrated under reduced pressure, respectively. After diethyl ether was added to the to the residue, the precipitates were collected by filtration and washed with diethyl ether to give powder (1.5 g. and 0.7 g.), respectively. These powder was combined together, 1.2 g. of which was dissolved in water and adjusted to pH 1 with dilute hydrochloric acid. (Total volume was about 20 ml.). The solution was subjected to column chromatography on "Amberite XAD-2" [Trademark: manufactured by Rohm and Haas Co.]. Water (400 ml.), 20% aqueous methanol (300 ml.), 50% aqueous methanol (400 ml.) and methanol (200 ml.) were passed through the column successively. Each eluate was detected with thin layer chromatography and the fractions containing the objective compound were combined and concentrated at 40° C. under reduced pressure to a volume of about 50 ml. The concentrate was lyophilized to give white powder of 7-[D-N-(DL-2-phenyl-2-sulfoacetyl)-2-phenylglycinamido]-cephalosporanic acid (0.7 g.). M.p. 88° C. (color changed), 250° C. (dec.).

I.R.: $\nu_{max}^{Nujol*}$: 1770 to 1790 (broad) cm$^{-1}$.

N.M.R.: δDMSO−d$_{6(ppm)}$: 2.0 (3H, s), 3.47 (2H, broad s), 4.4–5.1 (4H, m), 5.4–6.0 (2H, m), 7.0–7.7 (10H, m).

EXAMPLE 59

To a solution of 7-(D-2-phenylglycinamido)cephalosporanic acid (3.75 g.) and sodium bicarbonate (2.36 g.) in water (100 ml.) and acetone (50 ml.) was added dropwise a solution of D-2-(2,2,2-trichloroethoxycarbonylamino)-2-phenylacetyl chloride (3.53 g.) in acetone (10 ml.) with stirring under ice-cooling over 20 minutes. The solution was stirred at the same temperature for an hour, and the insoluble substance was collected by filtration, washed with acetone and dissolved in a mixture of ethyl acetate (200 ml.), acetone (10 ml.) and water (100 ml.). After shaking sufficiently, the ethyl acetate layer was separated and the aqueous layer was extracted three times with a mixture of ethyl acetate (200 ml.) and acetone (10 ml.). The extract and the ethyl acetate layer were combined together, washed with water (50 ml.) three times, dried over magnesium sulfate and then evaporated under reduced pressure. The residue was pulverized with diethyl ether, collected by filtration and dried to give colorless powder (3.9 g.) of 7-[D-N-{D-2-(2,2,2-trichloroethoxycarbonylamino)-2-phenylacetyl}-2-phenylglycinamido]cephalosporanic acid.

I.R.: $\nu_{max}^{Nujol*}$: 1798 cm$^{-1}$.

N.M.R.: δDMSO−d$_{6(ppm)}$: 1.97 (3H, s), 3.3, 3.54 (2H, AB−q, J=18 Hz), 4.71, 4.8 (2H, AB−q, J=16 Hz), 4.75 (2H, s), 4.94 (1H, d, J=5 Hz), 5.46 (1H, s), 5.6 (1H, s), 5.6 (1H, d, J=5 Hz), 7.26–7.55 (10H, m).

EXAMPLE 60

7-[D-N-{D-2-(2,2,2-trichloroethoxycarbonylamino)-2-phenylacetyl}-2-phenylglycinamido]cephalosporanic acid (2.85 g.), which was prepared in Example 59, was dissolved in N,N-dimethylformamide (28 ml.). Acetic acid (2.8 ml.) and zinc powder (2.85 g.) were added to the solution under ice-cooling and the mixture was stirred at the same temperature for an hour. After removing zinc powder by filtration, diethyl ether was added to the filtrate. The precipitating powder was collected by filtration and washed with acetone (40 ml.) to give pale yellow powder (2.46 g.) of 7-[D-N-(D-2-phenylglycyl)-2-phenylglycinamido]cephalosporanic acid. The product was suspended in water (50 ml.) and adjusted to pH 7.8 to 8.0 with 5% aqueous solution of sodium bicarbonate. After hydrogen sulfide gas was bubbled through the solution, the excess of hydrogen sulfide was removed by introducing nitrogen gas. The solution was adjusted to pH 7.8 to 8.0 with 5% aqueous solution of sodium bicarbonate and the insoluble substance was filtered off. The filtrate was adjusted to pH 5 to 6 with 10% hydrochloric acid and allowed to stand in a refrigerator, and the insoluble substance was filtered off. The filtrate was subjected to column chromatography on "Amberite XAD-2" [Trademark: manufactured by Rohm and Haas Co.] and eluted with water, 20% aqueous methanol and methanol, successively. The methanol eluate was concentrated under reduced pressure and ethanol was added to the residue. The ethanol solution was concentrated under reduced pressure to give the pure product.

M.p. 270° to 275° C. (dec.).

I.R.: $\nu_{max}^{Nujol*}$: 1760 cm$^{-1}$.

N.M.R.: $\delta$DMSO—d$_6$ $(ppm)$: 2.0 (3H, s), 3.1, 3.38 (2H, AB—q, J=17 Hz), 3.96 (3H, s), 4.7, 4.9 (2H, AB—q, J=15 Hz), 4.78 (1H, d, J=5 Hz), 5.04 (1H, s), 5.47 (1H, d, J=5 Hz), 5.64 (1H, s), 7.44–7.64 (10H, m).

EXAMPLE 61

A solution of 2-(2-hydroxyphenyl)acetic acid (1.68 g.) in thionyl chloride (10 ml.) was stirred at 60° C. for 1.5 hours and the excess of thionyl chloride was distilled off under reduced pressure. The residue containing the acid chloride was dissolved in dry acetone (10 ml.) and added dropwise to a solution of 7-(D-2-phenylglycinamido)-3-(1-methyl-1H-tetrazol-5-ylthiomethyl)-3-cephem-4-carboxylic acid (2.5 g.) and sodium bicarbonate (1.26 g.) in acetone (70 ml.) and water (70 ml.) with stirring under ice-cooling, meanwhile the solution was kept at pH 7.5 with 5% aqueous solution of sodium bicarbonate. After stirring the solution at the same temperature for an hour, the solvent was distilled off under reduced pressure. Ethyl acetate was added to the residue, adjusted to pH 2 with 10% hydrochloric acid and then shaken sufficiently. The ethyl acetate layer was separated, washed with water and a saturated aqueous solution of sodium chloride in turn, dried over magnesium sulfate and then evaporated under reduced pressure. Acetone (15 ml.) and a small amount of diethyl ether were added to the residue and stirred for 30 minutes. The precipitates were collected by filtration to give 7-[D-N-{2-(2-hydroxyphenoxy)acetyl}-2-phenylglycinamido]-3-(1-methyl-1H-tetrazol-5-ylthiomethyl)-3-cephem-4-carboxylic acid (2.3 g.). This product was purified by subjecting to column chromatography on activated charcoal (1.65 g.). M.p. 130° to 135° C. (dec.).

I.R.: $\nu_{max}^{Nujol*}$: 1780 cm$^{-1}$.

N.M.R.: $\delta$DMSO—d$_6$ $(ppm)$: 3.63 (2H, broad s), 3.93 (3H, s), 4.25 (2H, broad s), 4.6 (2H, s), 5.0 (1H, d, J=5 Hz), 5.6–5.85 (2H, m), 6.75–6.9 (4H, m), 7.3–7.5 (5H, m).

EXAMPLE 62

A solution of 2-(2-benzoyl-4-chlorophenoxy)acetic acid (1.44 g.) in thionyl chloride (7 ml.) was heated under reflux for 1.5 hours, and the excess of thionyl chloride was distilled off under reduced pressure. The residue containing the acid chloride was dissolved in dry acetone (20 ml.) and added dropwise to a solution of 7-[D-2-(3-mesylaminophenyl)glycinamido]-3-(1-methyl-1H-tetrazol-5-ylthiomethyl)-3-cephem-4-carboxylic acid (1.88 g.) and sodium bicarbonate (840 mg.) in water (120 ml.) and acetone (120 ml.) at 2° to 3° C. over 15 minutes, meanwhile the solution was kept at pH 7.0 to 7.5 with 5% aqueous solution of sodium bicarbonate. The solution was stirred at the same temperature for an hour and adjusted to pH 6 to 7, and acetone was distilled off under reduced pressure. The residue was washed with diethyl ether, and ethyl acetate was added to the residue and adjusted to pH 3 with 10% hydrochloric acid. After shaking sufficiently, the ethyl acetate layer was separated, washed with a saturated aqueous solution of sodium chloride, dried over magnesium sulfate and then evaporated under reduced pressure. Diethyl ether was added to the residue and stirred for an hour, and the precipitates were collected by filtration to give 7-[D-N-{2-(2-benzoyl-4-chlorophenoxy)acetyl}-2-(3-mesylaminophenyl)glycinamido]-3-(1-methyl-1H-tetrazol-5-ylthiomethyl)-3-cephem-4-carboxylic acid (1.75 g.).

I.R.: $\nu_{max}^{Nujol*}$: 1780 cm$^{-1}$.

N.M.R.: $\delta$DMSO—d$_6$+D$_2$O $(ppm)$: 3.0 (3H, s), 3.65 (2H, broad s), 4.0 (3H, s), 4.36 (2H, broad s), 4.63 (2H, s), 5.02 (1H, d, J=4 Hz), 5.57 (1H, s), 5.74 (1H, d, J=4 Hz), 7.08–7.9 (12H, m).

EXAMPLE 63

A solution of 2-(2-hydroxy-3,5-dichlorophenoxy)acetic acid (4.74 g.) in thionyl chloride (30 ml.) was stirred at 50° to 60° C. for 2.5 hours, and the excess of thionyl chloride was distilled off under reduced pressure. The residue containing the acid chloride was dissolved in dry acetone (20 ml.) and added dropwise to a solution of 7-(D-2-phenylglycinamido)-3-(1-methyl-1H-tetrazol-5-ylthiomethyl)-3-cephem-4-carboxylic acid (5.07 g.) and sodium bicarbonate (2.52 g.) in acetone (150 ml.) and water (100 ml.) with stirring under ice-cooling, meanwhile the solution was kept at pH 7 to 7.5 with 5% aqueous solution of sodium bicarbonate. The solution was stirred at the same temperature for an hour and acetone was distilled off under reduced pressure. After adding ethyl acetate to the residue, the solution was shaken sufficiently. The aqueous layer was separated, and ethyl acetate was added to the aqueous solution and adjusted to pH 3 with 10% hydrochloric acid. After shaking sufficiently, the ethyl acetate layer was separated, washed with water and a saturated aqueous solution of sodium chloride in turn, dried over magnesium sulfate and then evaporated under reduced pressure. The residue was pulverized with diethyl ether, collected by filtration and washed with diethyl ether to give 7-[D-N-{2-(2-hydroxy-3,5-dichlorophenoxy)acetyl}-2-phenylglycinamido]-3-(1-methyl-1H-tetrazol-5-ylthiomethyl)-3-cephem-4-carboxylic acid (3.8 g.). This product was dissolved in ethyl acetate and subjected to column chromatography on silica gel to give the powder, which was dissolved in distilled acetone and purified by subjecting to column chromatography on activated charcoal. M.p. 175° to 177° C. (dec.).

I.R.: $\nu_{max}^{Nujol*}$: 1778 cm$^{-1}$.

N.M.R.: $\delta$Acetone—d$_6$+D$_2$O$(ppm)$: 3.58, 3.83 (2H, AB—q), 4.02 (3H, s), 4.37 (2H, broad s), 4.83 (2H, s), 5.06 (1H, d, J=6 Hz), 5.82 (1H, d, J=6 Hz), 5.93 (1H, s), 7.03–7.08 (2H, m), 7.32–7.67 (5H, m).

EXAMPLE 64

7-(D-2-Phenylglycinamido)cephalosporanic acid (5.0 g.) was dissolved in a solution of sodium bicarbonate (3.15 g.) in acetone (75 ml.) and water (150 ml.). On the other hand 2-(2-formylphenoxy)acetic acid (3.38 g.) was dissolved in thionyl chloride and heated under reflux for an hour. The excess of thionyl chloride was distilled off under reduced pressure and the residue was dissolved in dry acetone. The acetone solution was added dropwise to the solution prepared above with stirring at 0° to −5° C. over 30 minutes, and the mixture was stirred at the same temperature for 2.5 hours. The insoluble substance was filtered off, and the filtrate was concentrated under reduced pressure. The concentrate was adjusted to pH 1 to 2 and extracted with ethyl acetate. The extract was concentrated under reduced pressure to give powder (3 g.). The powder (1.4 g.) was dissolved in acetone (16 ml.), and water (20 ml.) was added to the solution. The precipitates were collected by filtration to give 7-[D-N-{2-(2-formylphenoxy)acetyl}-2-phenylglycinamido]cephalosporanic acid (1.08 g.). M.p. 181° to 182° C. (dec.).

I.R.: $\nu_{max}^{Nujol*}$: 1783 cm$^{-1}$.

N.M.R.: δDMSO−d$_6$ $_{(ppm)}$: 2.0 (3H, s), 3.5 (2H, broad s), 4.67, 5.0 (2H, AB-q, J=14 Hz), 4.82 (2H, s), 5.02 (1H, d, J=5 Hz), 5.57–5.85 (2H, m), 6.9–7.8 (9H, m), 10.3 (1H, s).

EXAMPLE 65

A solution of o-nitrocinnamoyl chloride (0.3 g.) in dry acetone (10 ml.) was added dropwise to a solution of 7-(D-2-phenylglycinamido)cephalosporanic acid (0.5 g.) and sodium bicarbonate (0.4 g.) in water (20 ml.) and acetone (10 ml.) at 4° to 5° C. over 20 minutes, and the solution was stirred at the same temperature for 30 minutes and further at room temperature for 2 hours. After distilling off the acetone under reduced pressure, ethyl acetate (200 ml.) and water (200 ml.) were added to the residue. The solution was adjusted to pH 2 with 10% hydrochloric acid and the insoluble substance was filtered off. The ethyl acetate layer was separated from the filtrate and concentrated under reduced pressure to give 7-[D-N-(o-nitrocinnamoyl)-2-phenylglycinamido]cephalosporanic acid (0.5 g.). The product was purified by washing with ethyl acetate (360 mg.). M.p. 198° to 203° C. (dec.).

I.R.: $\nu_{max}^{Nujol*}$: 1780 cm$^{-1}$.

N.M.R.: δDMSO−d$_6$ $_{(ppm)}$: 2.02 (3H, s), 3.47 (2H, broad s), 4.63, 5.0 (2H, AB-q, J=18 Hz), 5.03 (1H, d, J=5 Hz), 5.6–5.9 (2H, m), 6.94 (1H, d, J=18 Hz), 7.2–8.1 (9H, m), 7.75 (1H, d, J=18 Hz).

EXAMPLE 66

Preparation of the starting compound (1) A solution of N-methyl-N-phenylsalicylamide (13.5 g.), ethyl bromoacetate (10 g.) and anhydrous potassium carbonate (8.4 g.) in N,N-dimethylformamide (90 ml.) was stirred at room temperature for 7 hours. The resultant mixture was added to water and extracted with diethyl ether, and the extract was washed with 10% aqueous solution of sodium hydroxide and water in turn, dried over magnesium sulfate and then evaporated under reduced pressure to give oily ethyl 2-[2-(N-methyl-N-phenylcarbamoyl)phenoxy]acetate (18.23 g.).

I.R.: $\nu_{max}^{Nujol*}$: 1750, 1650, 1595 cm$^{-1}$.

(2) Thus obtained ethyl 2-[2-(N-methyl-N-phenylcarbamoyl)phenoxy]acetate (18.23 g.) was added to 10% solution of potassium hydroxide in methanol (2 parts) and water (1 part), and the solution was stirred at room temperature for an hour and allowed to stand overnight. After concentrating the solution under reduced pressure, ethyl acetate was added to the concentrate. After shaking sufficiently, the aqueous solution was separated, acidified with 10% hydrochloric acid and extracted with ethyl acetate. The extract was washed with water, dried and concentrated under reduced pressure to give crystals (13.21 g.) of 2-[2-(N-methyl-N-phenylcarbamoyl)phenoxy]acetic acid.

M.p. 148° C.

I.R.: $\nu_{max}^{Nujol*}$: 2700 to 2500, 1740, 1610, 1580 cm$^{-1}$.

Preparation of the object compound

Thus obtained 2-[2-(N-methyl-N-phenylcarbamoyl)phenoxy]acetic acid (5.25 g.) was dissolved in a mixture of thionyl chloride (10 ml.) and N,N-dimethylformamide (one drop). Dry benzene was added to the solution and stirred with heating under reflux for an hour. After distilling off the solvent under reduced pressure, benzene was added to the residue and evaporated under reduced pressure. The residue containing the acid chloride was dissolved in dry acetone (30 ml.) and added dropwise to a solution of 7-(D-2-phenylglycinamido)cephalosporanic acid (5 g.) and sodium bicarbonate (3.1 g.) in water (25 ml.) and acetone (25 ml.) with stirring under ice-cooling. The solution was stirred at room temperature for an hour and then water was added to the solution, adjusted to pH 2 and extracted with ethyl acetate. The extract was dried over magnesium sulfate and evaporated under reduced pressure, and the residue was pulverized with diethyl ether and collected by filtration to give 7-[D-N-[2-{2-(N-methyl-N-phenylcarbamoyl)phenoxy}acetyl]-2-phenylglycinamido]cephalosporanic acid (5.8 g.).

I.R.: $\nu_{max}^{Nujol*}$: 3300, 1785, 1730, 1710, 1670, 1630 cm$^{-1}$.

N.M.R.: δDMSO−d$_6$ $_{(ppm)}$: 2.08 (3H, s), 3.39 (3H, s), 3.55 (2H, broad s), 4.51 (2H, broad s), 4.82 (2H, AB-q, J=14 Hz), 5.05 (1H, d, J=5 Hz), 5.6–6.0 (2H, m), 6.73–7.70 (14H, m), 8.40 (1H, d, J=8 Hz), 9.45 (1H, d, J=8 Hz).

EXAMPLE 67

A mixture of 2-(2-benzoyl-4-chlorophenoxy)acetic acid (2.15 g.), thionyl chloride (10 ml.), benzene (10 ml.) and N,N-dimethylformamide (one drop) was stirred at 70° C. for 2 hours and the solvent was distilled off under reduced pressure. The residue containing the acid chloride was dissolved in acetone and added dropwise to a solution of 7-(D-2-phenylglycinamido)cephalosporanic acid (2.0 g.) and sodium bicarbonate (1.33 g.) in acetone (30 ml.) and water (60 ml.) with stirring under ice-cooling over 30 minutes. After stirring at room temperature for 2 hours, ethyl acetate was added to the solution, adjusted to pH 2 with 10% hydrochloric acid under ice-cooling and the insoluble substance was filtered off. The filtrate was extracted with ethyl acetate twice and the extracts were washed with a saturated aqueous solution of sodium chloride and water in turn, dried over magnesium sulfate and evaporated under reduced pressure. The residue was pulverized with diethyl ether to give 7-[D-N-{2-(2-benzoyl-4-chlorophenoxy)acetyl}-2-phenylglycinamido]cephalosporanic acid (1.7 g.).

M.p. 117° C. (dec.).

I.R.: $\nu_{max}^{Nujol*}$: 3400, 3250, 1785, 1730, 1710, 1695, 1640 cm$^{-1}$.

N.M.R.: δDMSO−d$_6$ $_{(ppm)}$: 2.10 (3H, s), 3.61 (2H, broad s), 5.01 (2H, q, J=14 Hz), 5.18 (1H, d, J=5 Hz), 4.81 (2H, s), 5.7–6.3 (2H, m), 7.3–8.2 8H, m), 8.34 (1H, d, J=8 Hz), 9.28 (1H, d, J=8 Hz).

EXAMPLE 68

Preparation of the starting compound (1) 2-Hydroxy-5-chloro-4-nitrodiphenylketone (10 g.), methyl chloroacetate (5.85 g.), potassium carbonate (7.5 g.) and potassium iodide (200 mg.) were added to dry acetone (150 ml.), and heated under reflux for 3.5 hours. The insoluble substance was filtered off, and acetone was distilled off from the filtrate under reduced pressure. The residue was dissolved in ethyl acetate and shaken with 5% aqueous solution of sodium hydroxide (100 ml.). The ethyl acetate layer was separated, washed with a saturated aqueous solution of sodium chloride, dried over magnesium sulfate and then evaporated under reduced pressure. The residue was washed with petroleum ether to give methyl 2-[4-chloro-2-(4-nitrobenzoyl)phenoxy]acetate (11.7 g.).

I.R.: $\nu_{max}^{Nujol*}$: 1755, 1670 cm$^{-1}$.

(2) A 1 N aqueous solution of sodium hydroxide (35 ml.) was added to a solution of methyl 2-[4-chloro-2-(4-nitrobenzoyl)phenoxy]acetate (11.5 g.) in dioxane (60 ml.) and stirred at room temperature for 1.5 hours. Dioxane was distilled off under reduced pressure, and the residue was washed with ethyl acetate, adjusted to pH 1 with 10% hydrochloric acid and then extracted with ethyl acetate (each 400 ml. and 100 ml.). The extracts were washed with a saturated aqueous solution of sodium chloride, dried over magnesium sulfate and then concentrated under reduced pressure to a volume of about 100 ml. The precipitating crystals were collected by filtration to give 2-[4-chloro-2-(4-nitrobenzoyl)phenoxy]acetic acid (10.1 g.).

I.R.: $\nu_{max}^{Nujol*}$: 1750, 1740, 1640 cm$^{-1}$.

N.M.R.: $\delta D_2O + NaHCO_3$ $(ppm)$: 4.47 (2H, s), 6.9–7.6 (3H, m), 7.84, 8.16 (2H, AB-q, J=10 Hz, 20 Hz).

(3) 10% Palladium carbon (800 mg.) was added to a solution of 2-[4-chloro-2-(4-nitrobenzoyl)phenoxy]acetic acid (2.52 g.) in acetic acid (2.5 ml.) and dioxane (60 ml.), and then hydrogen gas (554 ml.) was absorbed in the mixture at room temperature under atmospheric pressure. After removing the insoluble substance by filtration, the solvent was distilled off from the filtrate under reduced pressure, and the residue was added to a solution of sodium bicarbonate (3.2 g.) in water (50 ml.) and acetone (50 ml.). Bromoacetyl chloride (2.36 g.) was added to the solution with stirring at 0° to 5° C. over 15 minutes, meanwhile the solution was kept at pH 7.0 to 7.5, and the solution was stirred at the same temperature for an hour. Acetone was distilled off under reduced pressure, and the residue was washed with ethyl acetate, adjusted to pH 1 with 10% hydrochloric acid and then extracted with ethyl acetate (each 70 ml. and 50 ml.). The extracts were washed with a saturated aqueous solution of sodium chloride, dried over magnesium sulfate, concentrated under reduced pressure to a volume of about 20 ml., and then allowed to stand in a refrigerator overnight to give 2-[4-chloro-2-(4-bromoacetamidobenzoyl)phenoxy]acetic acid (1.28 g.).

I.R.: $\nu_{max}^{Nujol*}$: 3390, 1765, 1745, 1670, 1630, 1590 cm$^{-1}$.

Preparation of the object compound

2-[4-Chloro-2-(4-bromoacetamidobenzoyl)phenoxy]acetic acid (1.2 g.) was added to thionyl chloride (12 ml.), and heated under reflux for an hour. Thionyl chloride was distilled off under reduced pressure, and the residue containing the acid chloride was dissolved in acetone (5 ml.) and added dropwise to a solution of 7-(D-2-phenylglycinamido)cephalosporanic acid (1.25 g.) and sodium bicarbonate (840 mg.) in water (70 ml.) and acetone (70 ml.) under ice-cooling. The solution was stirred at the same temperature for 30 minutes, meanwhile the solution was kept at pH 7.5 with 5% aqueous solution of sodium bicarbonate. Water (150 ml.) and ethyl acetate (150 ml.) were added to the resultant solution and adjusted to pH 2 with 10% hydrochloric acid, and the ethyl acetate layer was separated. The aqueous layer was extracted with ethyl acetate (70 ml.), and the extract and the ethyl acetate layer were combined together, washed with a saturated aqueous solution of sodium chloride, dried over magnesium sulfate and then evaporated under reduced pressure. The residue was crystallized with diethyl ether and collected by filtration to give 7-[D-N-2-{4-chloro-2-(4-bromoacetamidobenzoyl)phenoxy}acetyl-2-phenylglycinamido]cephalosporanic acid (1.82 g.).

I.R.: $\nu_{max}^{Nujol*}$: 3290, 1780, 1740, 1710, 1680, 1650 cm$^{-1}$.

EXAMPLE 69

A solution of 7-[D-N-[2-{2-(4-bromoacetamidobenzoyl)4-chlorophenyl}acetyl]-2-phenylglycinamido]cephalosporanic acid (1.63 g.) which was prepared in Example 68, mercaptoacetic acid (280 mg.) and sodium bicarbonate (670 mg.) in water (40 ml.) and acetone (15 ml.) was stirred at room temperature for 5 hours. The resultant solution was added to ice-water (50 ml.) and then ethyl acetate (70 ml.) was added to the solution, adjusted to pH 2 with 10% hydrochloric acid. After shaking sufficiently, the ethyl acetate layer was separated. The aqueous layer was extracted with ethyl acetate (50 ml.), and the extract was combined with the ethyl acetate layer, washed with a saturated aqueous solution of sodium chloride, dried over magnesium sulfate and then evaporated under reduced pressure. The residue was pulverized with diethyl ether and collected by filtration to give 7-[D-N-[2-{2-(4-carboxymethylthioacetamidobenzoyl)-4-chlorophenoxy}acetyl]-2-phenylglycinamido]cephalosporanic acid (1.58 g.). The product was purified by subjecting to column chromatography on silica gel [eluent: ethyl acetate (7)+acetic acid (1)]. M.P. 136° to 147° C. (dec.).

I.R.: $\nu_{max}^{Nujol*}$: 1760 to 1770 cm$^{-1}$.

N.M.R.: $\delta Acetone-d_6 + D_2O_{(ppm)}$: 2.05 (3H, s), 3.26–3.75 (6H, m), 4.68 (2H, s), 4.81, 5.06 (2H, AB-q, J=16 Hz), 5.06 (1H, d, J=5 Hz), 5.62 (1H, s), 5.8 (1H, d, J=5 Hz), 7.2–7.9 (9H, m).

EXAMPLE 70

A solution of 7-[D-N-(o-nitrocinnamoyl)-2-phenylglycinamido]cephalosporanic acid (580 mg.) which was prepared in Example 65, sodium bicarbonate (170 mg.) and 1-methyl-1H-tetrazole-5-thiol (140 mg.) in phosphate buffer (pH 6.4) (50 ml.) and acetone (25 ml.) was stirred at 60° C. for 10 hours. Acetone was distilled off under reduced pressure, and water (100 ml.) was added to the residue, washed with ethyl acetate, adjusted to pH 4 to 5 with dilute hydrochloric acid, and then extracted with ethyl acetate. The extract was washed with water, dried and concentrated under reduced pressure to give 7-[D-N-(o-nitrocinnamoyl)-2-phenylglycinamido]-3-(1-methyl-1H-tetrazol-5-ylthiomethyl)-3-cephem-4-carboxylic acid (330 mg.). The product was washed with diethyl ether and dissolved in acetone (4 ml.). An solution of sodium 2-ethylhexanoate in acetone (1.3 ml.) was added to the solution and the precipitating crystals were collected by filtration to give pale brown powder of the pure product. M.p. 169° to 180° C. (dec.).

I.R.: $\nu_{max}^{Nujol*}$: 1760 cm$^{-1}$.

N.M.R.: $\delta DMSO-d_6 + D_2O$ $(ppm)$: 3.5 (2H, broad s), 3.88 (3H, s), 4.25 (2H, broad s), 4.86 (1H, d, J32 5 Hz), 5.43 (1H, d, J=5 Hz), 5.75 (1H, s), 6.87 (1H, d, J=18 Hz), 7.6 (1H, d, J=18 Hz), 7.1–8.0 (9H, m).

EXAMPLE 71

A solution of 7-[D-N-[2-{2-N-methyl-N-phenylcarbamoyl)phenoxy}acetyl]-2-phenylglycinamido]cephalosporanic acid (3 g.), 1-methyl-1H-tetrazole-5-thiol (0.58 g.) and sodium bicarbonate (0.76 g.) in water (100 ml.) and acetone (50 ml.) was stirred at 65° to 70° C. for 6 hours, meanwhile the solution was kept at pH 7 to 7.2. After removing the insoluble substance by filtration, water was added to the filtrate to a total volume of 300 ml., treated with activated charcoal, adjusted to pH 2.0 with 10% hydrochloric acid under cooling and then extracted with ethyl acetate. The extract was washed with water and a saturated aqueous solution of sodium chloride in turn, dried over magnesium sulfate and then evaporated under reduced pressure the residue was crystallized with a small amount of ethyl acetate and collected by filtration to give 7-[D-N-[2-}2-(N-methyl-N-phenylcarbamoyl)phenoxy}acetyl]-2-phenylglycinamido]-3-(1-methyl-1H-tetrazol-5-ylthiomethyl)-3-cephem-4-carboxylic acid (0.69 g.).

I.R.: $\nu_{max}^{Nujol*}$: 3300, 1780, 1700, 1670, 1630 cm$^{-1}$.

N.M.R.: $\delta$DMSO—d$_6$ $_{(ppm)}$: 3.35 (3H, s), 3.92 (3H, s), 3.57 (2H, broad s), 4.2–4.55 (4H, m), 5.03 (1H, d, J=5 Hz), 5.55–5.92 (2H, m), 6.65–7.70 (14H m), 8.40 (1H, d, J=8 Hz), 9.45 (1H, d, J=8 Hz).

EXAMPLE 72

Preparation of the starting product

A calculated volume of hydrogen gas was absorbed in a solution of 2-[4-chloro-2-(4-nitrobenzoyl)phenoxy]acetic acid (5.0 g.), which was prepared in the preparation of the starting product (1) and (2) of Example 68, 10% palladium carbon (1.5 g.) in dioxane (100 ml.) at room temperature under atmospheric pressure. After removing the insoluble substance by filtration, the filtrate was added to a solution of sodium bicarbonate (3.4 g.) in water (100 ml.). To the solution was added dropwise a solution of chloroacetyl chloride (2.54 g.) in dry acetone (2 ml.) with stirring at 0° to 5° C., meanwhile the solution was kept at pH 7.0 to 7.5. The solution was stirred at the same temperature for an hour and dioxane was distilled off under reduced pressure. The residue was washed with ethyl acetate, adjusted to pH 1 with 10% hydrochloric acid, and extracted with ethyl acetate (each 150 ml. and 50 ml.). The extract was washed with a saturated aqueous solution of sodium chloride, dried over magnesium sulfate and evaporated under reduced pressure. The residue was washed with diethyl ether to give 2-[4-chloro-2-(4-chloroacetamidobenzoyl)phenoxy]acetic acid (4.4 g.).

I.R.: $\nu_{max}^{Nujol*}$: 3300, 1770, 1680, 1645, 1620, 1600 cm$^{-1}$.

Preparation of the object compound

2-[4-Chloro-2-(4-chloroacetamidobenzoyl)phenoxy]acetic acid (960 mg.) obtained above was added to thionyl chloride (10 ml.), heated under reflux for an hour, and then evaporated under reduced pressure. The residue containing the acid chloride was dissolved in dry acetone (5 ml.) and added to a solution of 7-[D-2-phenylglycinamido]cephalosporanic acid (1 g.) and sodium bicarbonate (630 mg.) in water (50 ml.) and acetone (50 ml.) at 0° to 5° C. over 15 minutes. The solution was stirred at the same temperature for 20 minutes, meanwhile the solution was kept at pH 7.0 to 7.5. The insoluble substance was filtered off and washed with water. The filtrate and the washing were combined together, and water (100 ml.) and ethyl acetate (150 ml.) were added to the solution, adjusted to pH 2 with 10% hydrochloric acid. The ethyl acetate layer was separated and the aqueous layer was extracted with ethyl acetate (50 ml.). The extract and the ethyl acetate layer were combined, washed with a saturated aqueous solution of sodium chloride and then evaporated under reduced pressure. The residue was pulverized with diethyl ether to give 7-[D-N-2-{4-chloro-2-(4-chloroacetamidobenzoyl)phenoxy}acetyl-2-phenylglycinamido]cephalosporanic acid (1.34 g.).

I.R.: $\nu_{max}^{Nujol*}$: 3400, 3380, 1790, 1740, 1710, 1675, 1655 cm$^{-1}$.

EXAMPLE 73

A solution of 7-[D-N-2-{-4-chloro-2-(4-chloroacetamidobenzoyl)phenoxy}acetyl-2-phenylglycinamido]cephalosporanic acid (1.15 g.), mercaptoacetic acid (0.21 g.) and sodium bicarbonate (510 mg.) in acetone (15 ml.) and water (30 ml.) was stirred at room temperature for 3.5 hours. Acetone was distilled off under reduced pressure, and the residue was adjusted to pH 1 with 10% hydrochloric acid and extracted with ethyl acetate (each 100 ml. and 50 ml.). The extracts were combined, washed with a saturated aqueous solution of sodium chloride, dried over magnesium sulfate and then evaporated under reduced pressure. The residue was pulverized with diethyl ether and collected by filtration to give 7-[D-N-2-{4-chloro-2-(4-carboxymethylthioacetamidobenzoyl)phenoxy}acetyl-2-phenylglycinamido]cephalosporanic acid (1.0 g.).

EXAMPLE 74

A solution of 2-(2-carbamoylphenoxy)acetic acid (0.975 g.), triethylamine (0.5 g.) and N,N-dimethylbenzylamine (3 drops) in methylene chloride (25 ml.) was added dropwise to a solution of isobutyl chloroformate (0.68 g.) in methylene chloride (50 ml.) at −15° to −10° C., and the solution was stirred at the same temperature for 40 minutes. To the solution was added all at once a solution of 7-(D-2-phenylglycinamido)-3-(1-methyl-1H-tetrazol-5-ylthiomethyl)-3-cephem-4-carboxylic acid (2.3 g.), bis(trimethylsilyl)acetamide (4.0 g.) in methylene chloride (50 ml.) at −30° C., and the solution was stirred at −30° to −20° C. for an hour, at −20° to −10° C. for 1.5 hour and then at 0° C. for an hour, successively. After the resultant solution was concentrated under reduced pressure ethyl acetate and an aqueous solution of sodium bicarbonate (50 ml.) were added to the residue and shaken sufficiently. The insoluble substance was collected by filtration and added to a mixture of water and ethyl acetate. The suspension was adjusted to pH 1 with 10% hydrochloric acid, and the ethyl acetate layer was separated, washed with water, dried over magnesium sulfate and then concentrated to give 7-[D-N-(2-carbamoylphenoxyacetyl)2-phenylglycinamido]-3-(1-methyl-1H-tetrazol-5-ylthiomethyl)3-cephem-4-carboxylic acid (1.10 g.). The product was purified by washing with a small amount of diethyl ether. M.p. 120° to 125° C. (dec.).

I.R.: $\nu_{max}^{Nujol*}$: 3300, 1780, 1700 (shoulder), 1650 cm$^{-1}$.

N.M.R.: $\delta$DMSO—d$_6$+D$_2$O$_{(ppm)}$: 3.61 (2H, s), 3.95 (3H, s), 4.28 (2H, s), 4.85 (2H, s), 5.02 (1H, d, J=5 Hz), 5.15 (1H, d, J=5 Hz), 5.25 (1H, s), 6.9–8.0 (9H, m).

EXAMPLE 75

A solution of 2-[2-(N-tert-butoxycarbonylaminomethyl)phenoxy]acetic acid (570 mg.), triethylamine (0.2 g.) and N,N-dimethylbenzylamine (3 drops) in methylene chloride (10 ml.) was added dropwise to a solution of isobutyl chloroformate (272 mg.) in methylene chloride at −15° to −10° C., and stirred at the same temperature for 45 minutes. To the solution was added all at once a solution of 7-(D-2-phenylglycinamido)-3-(1-methyl-1H-tetrazol-5-ylthiomethyl)-3-cephem-4-carboxylic acid (921 mg.) and bis(trimethylsilyl)acetamide (1.6 g.) in methylene chloride (20 ml.) at −35° C., and the solution was stirred at −30° to −20° C. for an hour, at −10° C. for an hour and then at 0° C. for an hour, successively. The resultant solution was concentrated under reduced pressure, and ethyl acetate and water were added to the residue, adjusted to pH 1 with 10% hydrochloric acid. After shaking sufficiently, the ethyl acetate layer was separated. An aqueous solution of sodium bicarbonate was added to the solution, and the precipitating crystals were collected by filtration, added to a mixture of water and ethyl acetate, adjusted to pH 1 with 10% hydrochloric acid and then shaken sufficiently. The ethyl acetate layer was separated, washed with water, dried over magnesium sulfate and then concentrated under reduced pressure to give 7-[D-N-{2-(N-tert-butoxycarbonylaminomethyl)phenoxyacetyl}-2-phenylglycinamido]-3-(1-methyl-1H-tetrazol-5-ylthiomethyl)-3-cephem-4-carboxylic acid (1.045 g.).

N.M.R.: δ Acetone−$d_6$+$D_2O_{(ppm)}$: 1.38 (9H, s), 3.67 (2H, s), 3.95 (3H, s), 4.30 (2H, s), 3.48 (2H, s), 4.00 (2H, s), 5.02 (1H, d, J=5 Hz), 5.80 (1H, d, J=5 Hz), 5.82 (1H, s), 6.9–7.6 (9H, m).

EXAMPLE 76

7-[D-N-{2-(N-tert-butoxycarbonylaminomethyl)phenoxyacetyl}-2-phenylglycinamido]-3-(1-methyl-1H-tetrazol-5-ylthiomethyl)-3-cephem-4-carboxylic acid (1.73 g.) was added to formic acid (17 ml.) and stirred at room temperature for an hour. Diethyl ether (50 ml.) was added to the resultant solution, and the precipitates were collected by filtration and washed with acetone to give 7-[D-N-(2-aminomethylphenoxyacetyl)-2-phenylglycinamido]-3-(1-methyl-1H-tetrazol-5-ylthiomethyl)-3-cephem-4-carboxylic acid (1.42 g.). The product was suspended in acetonitrile, and water (2 drops) was added to the solution. The precipitating crystals were collected by filtration to give the pure product. M.p. 160° to 170° C. (dec.).

I.R.: $\nu_{max}^{Nujol}$: 3300, 1770, 1645 cm$^{-1}$.

N.M.R.: δAcetone−$d_6$+$DCl_{(ppm)}$: 3.68 (2H, s), 4.00 (3H, s), 4.32 (4H, s), 5.00 (2H, s), 5.04 (1H, d, J=5 Hz), 6.75 (1H, s), 6.77 (1H, d, J=5 Hz), 7.0–7.7 (9H, m).

What we claim is:

1. A compound of the formula:

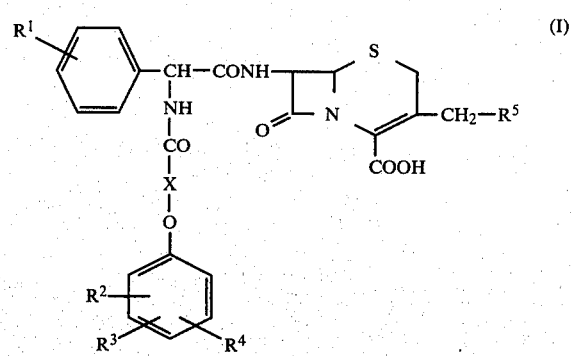

wherein
$R^1$ is hydrogen or lower alkanesulfonamido,
$R^2$ is hydroxy, carbamoyl, N-methyl-N-phenylcarbamoyl, amino(lower)alkyl, lower alkoxycarbonylamino(lower)alkyl or benzoyl,
$R^3$ and $R^4$ are each, same or different, hydrogen or halogen,
$R^5$ is lower alkyl tetrazolylthio, and
X is (lower)alkylene,
or the non-toxic pharmaceutically acceptable salt thereof.

2. A compound according to claim 1, which is 7-[D-N-[2-(2-hydroxyphenoxy)acetyl]-2-phenylglycinamido]-3-(1-methyl-1H-tetrazol-5-ylthiomethyl)-3-cephem-4-carboxylic acid.

3. A compound according to claim 1, which is 7-[D-N-[2-(2-hydroxy-3,5-dichlorophenoxy)acetyl]-2-phenylglycinamido]-3-(1-methyl-1H-tetrazol-5-ylthiomethyl)-3-cephem-4-carboxylic acid.

4. A compound according to claim 1, which is 7-[D-N-[2-[2-(N-methyl-N-phenylcarbamoyl)phenoxy]acetyl]-2-phenylglycinamido]-3-(1-methyl-1H-tetrazol-5-ylthiomethyl)-3-cephem-4-carboxylic acid.

5. A compound according to claim 1, which is 7-[D-N-(2-carbamoylphenoxyacetyl)-2-phenylglycinamido]3-(1-methyl-1H-tetrazol-5-ylthiomethyl)-3-cephem-4-carboxylic acid.

6. A compound according to claim 1, which is 7-[D-N-[2-(N-tert-butoxycarbonylaminomethyl)phenoxyacetyl]-2-phenylglycinamido]-3-(1-methyl-1H-tetrazol-5-ylthiomethyl)-3-cephem-4-carboxylic acid.

7. A compound according to claim 1, which is 7-[D-N-(2-aminomethylphenoxyacetyl)-2-phenylglycinamido]-3-(1-methyl-1H-tetrazol-5-ylthiomethyl)-3-cephem-4-carboxylic acid.

8. A compound according to claim 1, which is 7-[D-N-[2-(2-benzoyl-4-chlorophenoxy)acetyl]-2-(3-mesylaminophenyl)glycinamido]-3-(1-methyl-1H-tetrazol-5-ylthiomethyl)-3-cephem-4-carboxylic acid.

9. An antibacterial pharmaceutical composition comprising a therapeutically effective amount of the compound of claim 1 in association with a pharmaceutically acceptable, substantially non-toxic carrier or excipient.

* * * * *